US006869951B1

(12) United States Patent
Stallings et al.

(10) Patent No.: US 6,869,951 B1
(45) Date of Patent: Mar. 22, 2005

(54) METHOD OF CHANGING CONFORMATION OF A MATRIX METALLOPROTEINASE

(75) Inventors: William C. Stallings, Wildwood, MO (US); Huey S. Shieh, St. Louis, MO (US); Susan C. Howard, Fenton, MO (US); Gary A. DeCrescenzo, Dardeene Prairie, MO (US); Joseph J. McDonald, Wildwood, MO (US)

(73) Assignee: Pharmacia Corporation, St. Louis, MO (US)

( * ) Notice: Subject to any disclaimer, the term of this patent is extended or adjusted under 35 U.S.C. 154(b) by 52 days.

(21) Appl. No.: 10/031,181

(22) PCT Filed: Jul. 12, 2000

(86) PCT No.: PCT/US00/16323

§ 371 (c)(1),
(2), (4) Date: Jan. 16, 2002

(87) PCT Pub. No.: WO01/05389

PCT Pub. Date: Jan. 25, 2001

Related U.S. Application Data

(60) Provisional application No. 60/144,133, filed on Jul. 16, 1999.

(51) Int. Cl.⁷ .................. A61K 31/5377; C07D 295/14; A61P 19/02
(52) U.S. Cl. ..................................... 514/238.2; 544/159
(58) Field of Search .............................. 544/160, 159; 514/238.2

(56) References Cited

U.S. PATENT DOCUMENTS

| 4,595,700 A | 6/1986 | Donald et al. ............... 514/616 |
| 6,362,183 B1 | 3/2002 | Freskos et al. ........... 514/238.2 |
| 6,451,791 B1 * | 9/2002 | Heintz et al. ............. 514/238.2 |

FOREIGN PATENT DOCUMENTS

| EP | 0 757 037 A2 | 2/1997 | ......... C07C/311/42 |
| EP | 0 757 984 A1 | 2/1997 | ......... C07C/311/46 |
| EP | 0 780 386 A1 | 6/1997 | ......... C07D/309/08 |
| EP | 0 950 656 A1 | 10/1999 | ......... C07C/311/00 |
| JP | 11-236369 | 8/1999 | ......... C07C/311/45 |
| JP | 11-246527 | 9/1999 | ......... C07D/213/55 |
| WO | WO 90/05719 | 5/1990 | ......... C07C/323/62 |
| WO | WO 93/20047 | 10/1993 | ......... C07C/317/44 |
| WO | WO 94/02466 | 2/1994 | ......... C07D/221/14 |
| WO | WO 94/24140 | 10/1994 | ........... C07H/13/04 |
| WO | WO 95/09841 | 4/1995 | ......... C07C/323/60 |
| WO | WO 95/13289 | 5/1995 | ........... A61K/9/127 |
| WO | WO 95/29892 | 11/1995 | ....... C07D/207/327 |
| WO | WO 96/06074 | 2/1996 | ......... C07C/259/06 |
| WO | WO 97/20824 | 6/1997 | ......... C07D/241/04 |
| WO | WO 97/24117 | 7/1997 | .......... A61K/31/19 |
| WO | WO 98/03166 | 1/1998 | .......... A61K/31/18 |
| WO | WO 98/39315 | 9/1998 | ......... C07D/309/08 |
| WO | WO 98/39329 | 9/1998 | ......... C07D/413/12 |
| WO | WO 99/42433 | 8/1999 | ......... C07C/201/08 |

OTHER PUBLICATIONS

Reinemer et al., *Structural Implifications for the role of the N terminus in the 'superactivation' of collagenases*, FEBS Letters, 338:227–233 (1994).

Brünger, *Free R value: a novel statistical quantity for assessing the accuracy of crystal structures*, Nature, 355:472–475 (1992).

Denis et al., *Matrix metalloproteinase Inhibitors: Present achievements and future prospects*, Investig. New Drugs, 15:175–185 (1997).

Gearing et al., *Processing of tumour necrosis factor–α precursor by metalloproteinases*, Nature, 370:555–557 (1994).

Grams et al., *X–ray structures of human neutrophil collagenase complexed with peptide hydroxamate and peptide thiol Inhibitors—Implications for substrate binding and rational drug design*, Eur. J. Biochem., 228:830–841 (1995).

Jones et al., *Improved methods for building protein models in electron density maps and the location of errors in these models*, Acta Cryst., A47:110–119 (1991).

Kiyama et al., *Homology modeling of gelatinase catalytic domains and docking simulations of novel sulfonamide inhibitors*, J. Med. Chem., 42:1723–1738 (1999).

Lovejoy et al., *Crystal structures of MMP–1 and –13 reveal the structural basis for selectivity of collagenase inhibitors*, Nat. Struc. Biol., 6(3):217–221 (1999).

McGeehan et al., *Regulation of tumour necrosis factor–α processing by a metalloproteinase inhibitor*, Nature, 370:558–561 (1994).

(List continued on next page.)

Primary Examiner—Robert W. Ramsuer
Assistant Examiner—Kamal Saeed
(74) Attorney, Agent, or Firm—Harness Dickey & Pierce, P.L.C.

(57) ABSTRACT

The present invention provides a matrix metalloproteinase inhibiting compound having structure (VIII) or a salt, an enantiomer, a diastereomer, a racemate, or a tautomer thereof. In other embodiments, the present invention provides a method of changing the conformation of a matrix metalloproteinase, a method of inhibiting a matrix metal metalloproteinase, and a method of treating osteoarthritis.

(VIII)

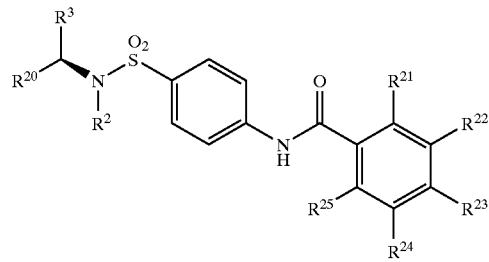

29 Claims, 5 Drawing Sheets

OTHER PUBLICATIONS

Mitchell et al., *Cloning, expression, and type II collagenolytic activity of matrix metalloproteinase–13 from human osteoarthritic cartilage*, J. Clin. Invest., 97(3):761–768 (1996).

Morgunova et al., *Structure of human pro–matrix metalloproteinase–2: Activation mechanism revealed*, Science, 284:1667–1670 (1999).

Nicholls et al., *Protein folding and association: Insights from the Interfacial and thermodynamic properties of hydrocarbons*, Proteins, 11(4) 281–296 (1991).

Otwinowski, *Oscillation data reduction program*, in Proceedings of CCP–4 Study Weekend: Data Collection and Processing, 56–62 (1993).

Parks et al., Matrix Metalloproteinases, 32–33 (1998).

Rasmussen et al., *Matrix metalloproteinase inhibition as a novel anticancer strategy: A review with special focus on batimastat and marimastat*, Pharmacol. Ther., 75(1):69–75 (1997).

Reboul et al., *The new collagenase, collagnease–3, is expressed and synthesized by human chondrocytes but not by synoviocytes*, J. Clin. Invest., 97(9):2011–2019 (1996).

Schwartz et al., *Synthetic inhibitors of bacterial and mammalian interstitial collagenases*, Prog. in Med. Chem., 29:271–334 (1992).

Tamura et al., *Highly selective and orally active inhibitors of type IV collagenase (MMP–9 and MMP–2); N–sulfonylamino acid derivatives*, J. Med. Chem., 41:640–649 (1998).

PCT/US00/16323 (WO 01/05389) International Search Report and Transmittal, 9 pgs.

* cited by examiner

Sequence Alignment for mmp-8, mmp-3, and mmp-1

```
              85     90       100       110       120
h-mmp8    NPKWERTNLTYRIRNYTPQLSEAEVERAIKDAFELWSVAS
h-mmp3    IPKWRKTHLTYRIVNYTPDLPKDAVDSAVEKALKVWEEVT
h-mmp1    NPRWEQTHLTYRIENYTPDLPRADVDHAIEKAFQLWSNVT
          *.* .*.***** ****.*.   *. *.   *.  .*  .

130       140       150       160
h-mmp8    PLIFTRISQGEADINIAFYQRDHGDNSPFDGPNGILAHAF
h-mmp3    PLTFSRLYEGEADIMISFAVREHGDFYPFDGPGNVLAHAY
h-mmp1    PLTFTKVSEGQADIMISFVRGDHRDNSPFDGPGGNLAHAF
          ** *... .*.*** *.*   .* * *****    ****.

170       180       190       200
h-mmp8    QPGQGIGGDAHFDAEETWTNTSANYNLF LVAAHEF GHSLG
h-mmp3    APGPGINGDAHFDDDEQWTKDTTGTNLF LVAAHEI GHSLG
h-mmp1    QPGPGIGGDAHFDEDERWTNNFREYNLH RVAAHEL GHSLG
          **** ****** .* **.        **  ***** .*****

210       220       230       240
h-mmp8    LAHSSDP GALMYPNY-AFRETSNYSLP QDDIDGIQAIYG
h-mmp3    LFHSANT EALMYPLYHSLTDLTRFRLS QDDINGIQSLYG
h-mmp1    LSHSTDI GALMYPSY-TF--SGDVQLA QDDIDGIQAIYG
          * **..  *****  *         *.****.***..**
```

FIG.1

| INTERACTING RESIDUES WITHIN 5 A OF THE INHIBITOR MOLECULE | | | | | | |
|---|---|---|---|---|---|---|
| | | XII | IX | X | XI | XIV |
| | L119 | NO | | | | NO |
| | G158 | | | | | |
| | I159 | | | | | |
| | L160 | | | | | |
| | A161 | | | | | |
| | H162 | | | | | |
| | A163 | NO | | | | |
| | L193 | | | | | |
| | V194 | | | | | |
| | A196 | NO | NO | | NO | NO |
| | H197 | | | | | |
| | E198 | | | | | |
| | H201 | | | | | |
| | H207 | | | | | |
| | G212 | | NO | NO | | NO |
| | A213 | | | | | |
| | L214 | | | | | |
| | Y216 | | | | | |
| | P217 | | | | | |
| | N218 | | | | | |
| | Y219 | | | | | |
| | A220 | | | | | |
| | R222 | | | | | |
| | T224 | NO | | | | NO |
| | Y227 | | NO | NO | NO | NO |
| | S228 | NO | | | | NO |
| | P230 | | | | | NO |

FIG. 2

Surrounding Residues in mmp8 Active Site
(Inhibitors XII and IX)

Surrounding Residues in mmp8 Active Site
(Inhibitors XII and XI)

($\phi, \psi$) DISTRIBUTION AMONG THE RESIDUES FROM 222 TO 231

| | 222(R) | | 223(E) | | 224(T) | | 225(S) | | 226(N) | |
|---|---|---|---|---|---|---|---|---|---|---|
| I | −143.1 | 145.4 | −50.0 | 128.2 | −102.1 | −14.3 | −48.1 | −31.1 | −147.0 | 43.3 |
| II | −132.7 | 133.2 | −76.8 | 126.3 | −112.1 | 134.8 | −124.7 | −16.2 | −145.6 | −174.7 |
| III | −154.5 | 134.9 | −73.5 | 145.4 | −141.2 | 115.8 | −89.0 | −23.2 | −136.0 | −161.4 |
| IV | −142.1 | 129.3 | −74.5 | 134.3 | −125.4 | 149.0 | −128.8 | −10.4 | −144.1 | −168.4 |
| X1 | −151.0 | 145.4 | −48.5 | 130.0 | −105.1 | −10.5 | −55.9 | −29.2 | −144.8 | 45.9 |
| X2 | −156.8 | 143.9 | −43.9 | 129.5 | −108.0 | −9.7 | −54.9 | −29.8 | −145.1 | 40.5 |

| | 227(Y) | | 228(S) | | 229(L) | | 230(P) | | 231(Q) | |
|---|---|---|---|---|---|---|---|---|---|---|
| I | −66.4 | 137.6 | −139.7 | 147.8 | −48.4 | 124.5 | −60.7 | 152.7 | −46.1 | −44.3 |
| II | −91.6 | 28.1 | −86.5 | 126.1 | −96.1 | 149.1 | −59.7 | 152.2 | −54.4 | −35.0 |
| III | −99.2 | 28.6 | −92.2 | 127.0 | −90.6 | 149.7 | −61.1 | 155.6 | −55.0 | −42.0 |
| IV | −97.7 | 21.7 | −85.3 | 128.3 | −85.4 | 159.9 | −62.8 | 156.6 | −56.3 | −40.1 |
| X1 | −74.2 | 143.6 | −143.0 | 153.8 | −54.7 | 138.0 | −66.6 | 158.4 | −46.3 | −51.6 |
| X2 | −70.4 | 140.5 | −138.9 | 157.2 | −54.4 | 136.8 | −67.6 | 157.8 | −46.1 | −50.5 |

FIG.5

METHOD OF CHANGING CONFORMATION OF A MATRIX METALLOPROTEINASE

This patent claims priority as a national-phase application of PCT Patent Application No. PCT/US00/16323 (Int'l Filing Date Jul. 12, 2000; WIPO Int'l Publ. No. WO 01/05389; Int'l Publ. Date Jan. 25, 2001 (in English)), which, in turn, claims priority to U.S. Provisional Patent Application Ser. No. 60/144,133 (filed Jul. 16, 1999). The entire texts of both those patent applications are incorporated by reference into this patent.

BACKGROUND OF THE INVENTION

1. Field of the Invention

This invention relates to matrix metalloproteinase enzymes, inhibitors of matrix metalloproteinase enzymes, and to methods of changing the conformation of matrix metalloproteinase enzymes.

2. Description of Related Art

Connective tissue, extracellular matrix constituents, and basement membranes are required components of all mammals, including humans. These components are the biological materials that provide rigidity, differentiation, attachments, and, in come cases, elasticity to biological systems. Connective tissue components include, for example, collagen, elastin, proteoglycans, fibronectin, and laminin. These biochemicals make up or are components of structures such as skin, bone, teeth, tendons, cartilage, basement membranes, blood vessels, cornea, and vitreous humor.

Under normal conditions, connective tissue turnover or repair processes are controlled and in equilibrium. The loss of this balance for whatever reason leads to a number of disease states. Inhibition of the enzymes responsible for loss of equilibrium provides a control mechanism for this tissue decomposition and, therefore, a treatment for these diseases.

Degradation of connective tissue or connective tissue components is carried out by the action of proteinase enzymes released from resident tissue cells or invading inflammatory or tumor cells. A major class of enzymes involved in this function includes the matrix metalloproteinase (MMP) enzymes. The MMPs are the subject of extensive study because of their potential involvement in disease mechanisms. Parks and Mecham have extensively reviewed the MMPs (*Matrix Metalloproteinases*, W. C. Parks and R. P. Mecham, ed., Academic Press, San Diego (1998)).

The MMPs are divided into classes with some members having several different names in common use. Examples are: collagenase I (MMP-1, fibroblast collagenase, EC 3.4.24.3); collagenase II (MMP-8, neutrophil collagenase, EC 3.4.24.34); collagenase III (MMP-13); stromelysin 1 (MMP-3, EC 3.4.24.17); stromelysin 2 (MMP-10, EC 3.4.24.22); proteoglycanase; matrilysin (MMP-7, EC 3.4.25.33); gelatinase A (MMP-2, 72 kDa gelatinase, EC 3.4.24.24); gelatinase B (MMP-9, 92 kDa gelatinase, EC 3.4.24.35); stromelysin 3 (MMP-11); metalloelastase (MMP-12, HME, human macrophage elastase, EC 3.4.24.65); MT1-MMP (MMP-14); MT2-MMP (MMP-15); MT3-MMP (MMP-16); and MT4-MMP (MMP-17).

The uncontrolled breakdown of connective tissue by MMPs is a feature of many pathological conditions. Examples include rheumatoid arthritis, osteoarthritis, septic arthritis, ulcerations (such as corneal, epidermal, or gastric ulcerations), periodontal disease, proteinuria; Alzheimer's Disease, coronary thrombosis, psoriasis, aneurysm, and bone disease. Defective injury repair processes also occur. This can produce improper wound healing leading to weak repairs, adhesions, and scarring. These latter defects can lead to disfigurement and/or permanent disabilities as with post-surgical adhesions.

MMP-8 (also known as neutrophil collagenase) has been shown to degrade type II collagen and aggrecan (a structural glycosaminoglycan found in the cartilage). MMP-8 has been found to be present in patients having osteoarthritis and rheumatoid arthritis and may participate significantly in the progression of these diseases. *Matrix Metalloproteinases*, W. C. Parks and R. P. Mecham, ed., Academic Press, San Diego (1998), pp. 32–33.

MMPs are also involved in the biosynthesis of tumor necrosis factor (TNF). Inhibition of the production or action of TNF and related compounds is a useful clinical disease treatment mechanism. TNF-$\alpha$, for example, is a cytokine that is believed to be produced initially as a 28 kDa cell-associated molecule. It is released as an active, 17 kDa form that can mediate many deleterious effects in vitro and in vivo. For example, TNF can cause or contribute to the effects of inflammation, rheumatoid arthritis, autoimmune disease, multiple sclerosis, graft rejection, fibrotic disease, cancer, infectious diseases, malaria, mycobacterial infection, meningitis, fever, psoriasis, cardiovascular/pulmonary effects (such as post-ischemic reperfusion injury, congestive heart failure hemorrhage, coagulation, and hyperoxic alveolar injury), radiation damage, and acute phase responses like those seen with infections and sepsis during shock such as septic shock and hemodynamic shock. Chronic disease of active TNF can cause cachexia and anorexia. Chronic release of TNF can be lethal.

TNF-$\alpha$ convertase is a metalloproteinase involved in the formation of active TNF$\alpha$. Inhibition of TNF-$\alpha$ convertase inhibits production of active TNF-$\alpha$. Some compounds that inhibit TNF-$\alpha$ convertase and MMPs involved in TNF-$\alpha$ biosynthesis are disclosed in PCT Patent Application No. WO 94/24140. Additional compounds that inhibit such enzymes are disclosed in PCT Patent Application No. WO 94/02466. Further inhibitors are disclosed in PCT Patent Application No. WO 97/20824.

Some compounds that inhibit certain MMPs have been shown to also inhibit the release of TNF (Gearing et al., Nature, 376, 555–557 (1994)). McGeehan et al. disclosed further compounds which inhibit MMPs and inhibit the release of TNF (Nature, 376, 558–561 (1994)). There remains a need for effective MMP and TNF-$\alpha$ convertase-inhibiting agents.

MMPs are involved in other biochemical processes as well. Included are the control of ovulation, post-partum uterine involution, possibly implantation of fertilized ova, cleavage of APP ($\beta$-Amyloid Precursor Protein) to the amyloid plaque and inactivation of $\alpha_1$-protease inhibitor ($\alpha_1$-PI). Inhibition of these Metalloproteinases permits, for example, the control of fertility and the treatment or prevention of Alzheimer's Disease. In addition, increasing and maintaining the levels of an endogenous or administered serine protease inhibitor drug or biochemical such as $\alpha_1$-PI supports the treatment and prevention of diseases such as emphysema, pulmonary diseases, inflammatory diseases, and diseases of aging such as loss of skin or organ stretch and resiliency.

Inhibition of selected MMPs can also be desirable in other instances. For example, selective inhibition of MMP-3, MMP-2, MMP-9, or MMP-13 in the presence of MMP-1 may be useful for the treatment of cancer, prevention of metastasis of cancer cells, or the inhibition of angiogenesis. A therapy which does not inhibit MMP-1 but does selectively inhibit one or more of the other MMPs can have a therapeutically useful profile.

Osteoarthritis, another prevalent disease wherein it is believed that cartilage degradation in flamed joints is at least partially caused by MMP-13 released from cells such as stimulated chrondrocytes, may be best treated by administration of drugs which selectively inhibit MMP-13. See, for example, Mitchell et al., *J. Clin. Invest.*, 97, 761–768 (1996). See also Reboul et al., J. Clin. Invest., 97, 2011–2019 (1996).

Some inhibitors of MMPs are known. Examples include natural biochemicals such as tissue inhibitor of metalloproteinase (TIMP), $a_2$-macroglobulin, and their analogs or derivatives. These are high molecular weight protein molecules that form inactive complexes with Metalloproteinases.

Some smaller peptide-like compounds that inhibit MMPs have also been described. Thiol group-containing amide or peptidyl amide-based metalloproteinase (MMP) inhibitors are known as is shown in, for example, PCT Patent Application No. WO 95/12389. Further such inhibitors are described in PCT Patent Application No. WO 97/24117. Still further such inhibitors are shown in U.S. Pat. No. 4,595,700. Hydroxamate group-containing MMP inhibitors are disclosed in a number of individual patent applications such as each of the following:

WO 95/29892.
WO 97/24117.
EP 0 780 386.
WO 90/05719.
WO 93/20047.
WO 95/09841.
WO 96/06074.

Swartz et al. disclose some peptidomimetic MMP inhibitors in *Progr. Med. Chem.*, 29, 271–334 (1992). Further peptidomimetic MMP inhibitors are disclosed by Rasmussen et al., in *Pharmacol. Ther.*, 75(1), 69–75 (1997). Denis et al., disclose further peptidomimetic MMP inhibitors in *Invest. New Drugs*, 15(3), 175–185 (1997).

One possible problem associated with many known MMP inhibitors is that they often exhibit the same or similar inhibitory effects against each of the MMP enzymes. In other words, many known MMP inhibitors are not very selective. For example, the peptidomimetic hydroxamate known as batimastat is reported to exhibit $IC_{50}$ values of about 1 to about 20 nanomolar (nM) against each of MMP-1, MMP-2, MMP-3, MMP-7, and MMP-9. Marimastat, another peptidomimetic hydroxamate, was reported to be another broad-spectrum MMP inhibitor with an enzyme inhibitory spectrum similar to batimastat, except that marimastat exhibits an $IC_{50}$ value against MMP-3 of about 230 nM. (Rasmussen et al., *Pharmacol. Ther.*, 75(1), 69–75 (1997))

Meta analysis of data from Phase I/II studies using marimastat in patients with advanced, rapidly progressive, treatment-refractory solid tumor cancers (colorectal, pancreatic, ovarian, prostate) indicated a dose-related reduction in the rise of cancer-specific antigens used as surrogate markers for biological activity. The most common drug-related toxicity of marimastat in those clinical trials was musculoskeletal pain and stiffness, often commencing in the small joints and the hands, spreading to the arms and shoulder. A short dosing holiday of 1–3 weeks followed by dosage reduction permitted treatment to continue. (Rasmussen et al., *Pharmacol. Ther.*, 75(1), 69–75 (1997))It is thought that the lack of specificity of inhibitory effect among the MMPs may be the cause of that effect.

The primary, secondary, and tertiary structures of the MMPs have a number of characteristic features. Each MMP contains a catalytic domain which in turn comprises a zinc binding site and an adjacent site known as the $S_1'$ pocket. The $S_1'$ pocket has been recognized as a major factor in substrate specificity of the MMPs. See for example B. Lovejoy et al., *Nat. Struct. Biol.*, 6 (3), 217–221 (1999) at 218. The $S_1'$ pocket is sometimes known as the specificity pocket.

FIG. 1 shows a partial sequence alignment for MMP-1, MMP-3, and MMP-8. The amino acid residues in the shaded boxes of FIG. 1 comprise the residues included in the $S_1'$ pocket for each of these MMPs. Symbols in FIG. 1 identifying the amino acid residues are commonly used by those of skill in the art. The primary, secondary, and tertiary structures work together for each MMP to provide the catalytic activity, kinetics, and substrate specificity of the enzyme. These structures define the shape or conformation of the amino acid residue backbone of the enzyme. The actual sequence of amino acid residues in the $S_1'$ pocket and the conformation of the residue backbone determine the specificity and kinetics of each MMP.

Some X-ray crystallographic experiments on MMPs are reported in the literature. For example, F. Grams et al. (Euro J. Biochem., 228, 830–841 (1995)) discloses X-ray structures of human neutrophil collagenase complexed with peptidomimetic hydroxamate and thiol inhibitors. In another report B. Lovejoy et al. (*Nat. Struct. Biol.*, 6 (3), 217–221 (1999)) disclose X-ray crystal structures of the catalytic domains of MMP-1 and MMP-13. Lovejoy et al. report that the MMP-1 S1' pocket undergoes a conformational change to accommodate certain diphenylether inhibitors but that the MMP-13 S1' pocket is larger and can accommodate the diphenylether inhibitors without undergoing a conformational change. They report that this difference determines the selectivity of these diphenylether compounds for preferentially inhibiting MMP-13 relative to MMP-1. The X-ray crystal structure for MMP-2 was reported by E. Morgunova et al. ("Structure of Human Pro-Matrix Metalloproteinase-2: Activation Mechanism Revealed," *Science* 284, 1667–1670 (1999)).

SUMMARY OF THE INVENTION

In view of the importance of MMP inhibitors in the treatment of several diseases and the lack of enzyme specificity exhibited by two of the more potent drugs now in clinical trials, it would be a great benefit if a new method were discovered by which to inhibit one or more MMP enzymes.

Among its several embodiments, the present invention provides a matrix metalloproteinase inhibiting compound having the structure:

Formula VIII

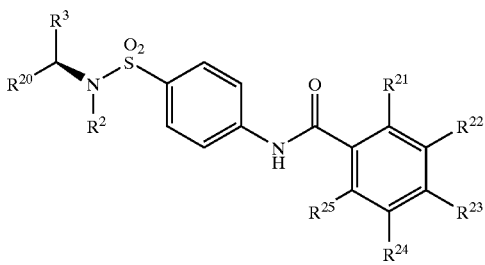

or a salt, an enantiomer, a diastereomer, a racemate, or a tautomer thereof, wherein: $R^2$ is selected from the group consisting of H, alkyl, alkenyl, alkynyl, cycloalkyl, haloalkyl, alkylaryl, arylalkyl, alkoxyalkyl, hydroxyalkyl, aminoalkyl, alkylaminoalkyl, heterocycloalkyl, and heterocycloalkylalkyl; $R^3$ is selected from the group consisting of H, alkyl, alkenyl, alkynyl, cycloalkyl, haloalkyl, alkylaryl, arylalkyl, alkoxy, alkoxyalkyl, hydroxyalkyl, aminoalkyl, alkylaminoalkyl, and heterocycloalkyl; $R^{20}$ is selected from the group consisting of —C(O)OH, —C(O)NHOH, —SH, and —C(O)SH; and $R^{21}$, $R^{22}$, $R^{23}$, $R^{24}$, and $R^{25}$ are independently selected from the group consisting of H, $C_1$ to about $C_{20}$ alkyl, $C_1$ to about $C_{20}$ alkenyl, $C_1$ to about $C_{20}$ alkynyl, cycloalkyl, haloalkyl, alkoxyalkyl, hydroxyalkyl, aminoalkyl, alkylaminoalkyl, nitroalkyl, heterocycloalkyl, and carboxyalkyl.

The invention is further directed to a method of changing the conformation of a matrix metalloproteinase wherein the method comprises contacting the matrix metalloproteinase with a compound having the formula:

Figure XIII

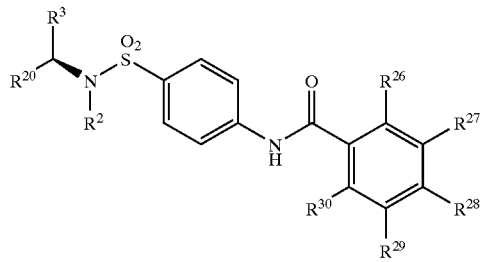

or a salt, an enantiomer, a diastereomer, a racemate, or a tautomer thereof, thereby changing the conformation of the matrix metalloproteinase, wherein: $R^2$ is selected from the group consisting of H, alkyl, alkenyl, alkynyl, cycloalkyl, haloalkyl, alkylaryl, arylalkyl, alkoxyalkyl, hydroxyalkyl, aminoalkyl, alkylaminoalkyl, heterocycloalkyl, and heterocycloalkylalkyl; $R^3$ is selected from the group consisting of H, alkyl, alkenyl, alkynyl, cycloalkyl, haloalkyl, alkylaryl, arylalkyl, alkoxy, alkoxyalkyl, hydroxyalkyl, aminoalkyl, alkylaminoalkyl, and heterocycloalkyl; $R^{20}$ is selected from the group consisting of —C(O)OH, —C(O)NHOH, —SH, and —C(O)SH; and $R^{26}$, $R^{27}$, $R^{28}$, $R^{29}$, and $R^{30}$ are independently selected from the group consisting of about $C_3$ to about $C_{20}$ alkyl, about $C_3$ to about $C_{20}$ alkenyl, about $C_3$ to about $C_{20}$ alkynyl, cycloalkyl, haloalkyl, alkoxyalkyl, hydroxyalkyl, aminoalkyl, alkylaminoalkyl, nitroalkyl, heterocycloalkyl, and carboxyalkyl.

The present invention is further provides a method of inhibiting a matrix metalloproteinase wherein the method comprises contacting the matrix metalloproteinase with a compound having the structure of Formula VIII or a salt, an enantiomer, a diastereomer, a racemate, or a tautomer thereof, thereby inhibiting the matrix metalloproteinase.

The present invention further provides a method of treating osteoarthritis in a mammal wherein the method comprises providing to the mammal an osteoarthritis-treating-effective amount of a compound having the structure of Formula VIII or an enantiomer, diastereomer, racemate, or tautomer thereof, thereby treating osteoarthritis.

Further scope of the applicability of the present invention will become apparent from the detailed description provided below. However, it should be understood that the following detailed description and examples, while indicating preferred embodiments of the invention, are given by way of illustration only since various changes and modifications within the spirit and scope of the invention will become apparent to those skilled in the art from this detailed description.

BRIEF DESCRIPTION OF THE FIGURES

FIG. 1 shows a partial sequence alignment for MMP-1, MMP-3, and MMP-8.

FIG. 2 shows MMP-8 S1' amino acid backbone residues which reside within 5 Å of a complexed inhibitor molecule.

FIG. 5 shows the (φ,ψ) distribution among the amino acid residues of MMP-8 from 222 to 231.

DETAILED DESCRIPTION OF THE PREFERRED EMBODIMENTS

Figure 3:
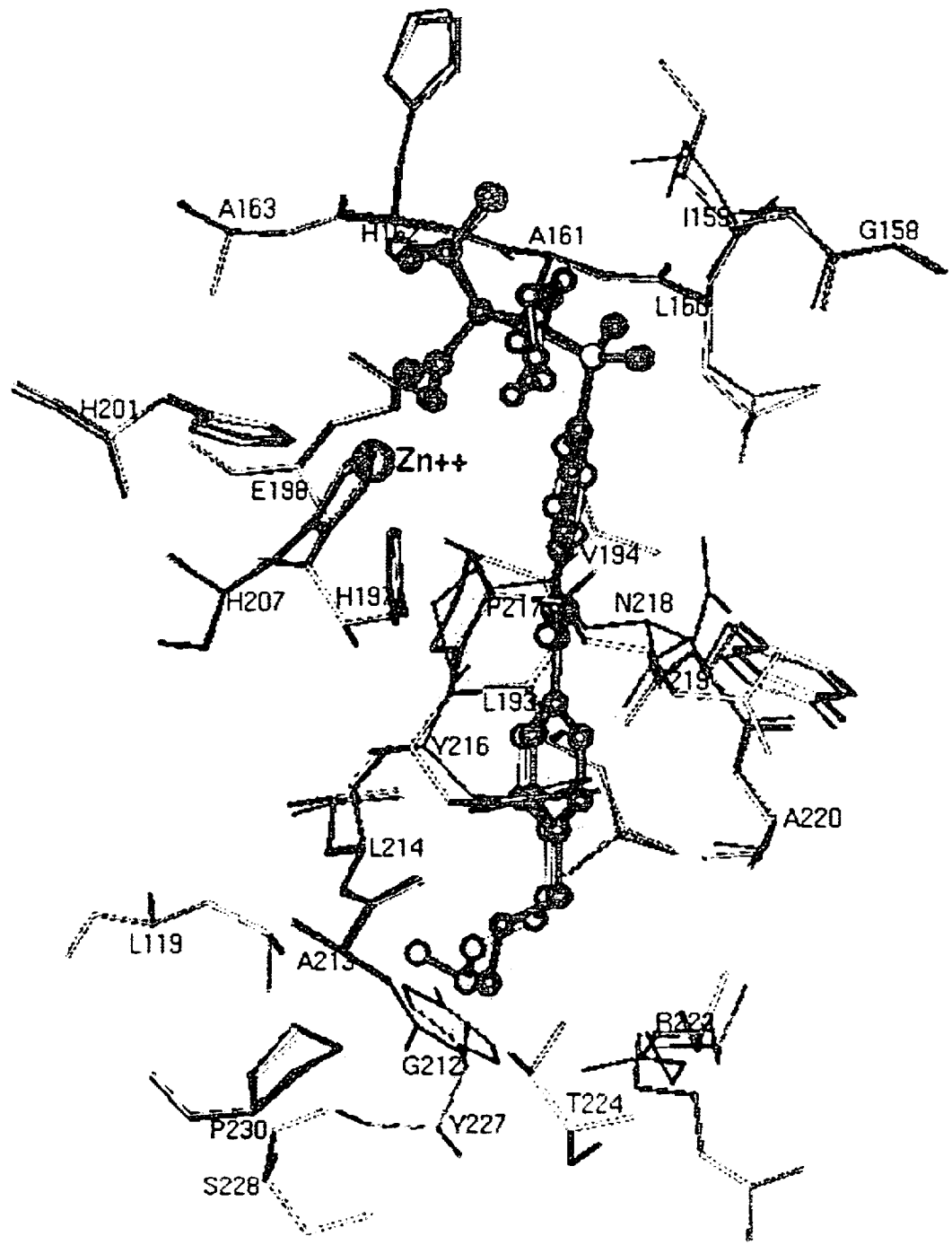
FIGS. 3 and 4 show the effect of progressively lengthening the P1' group of an MMP inhibitor on the conformation of the substituents on amino acid residues of the S1' pocket.

The following detailed description is provided to aid those skilled in the art in practicing the present invention. Even so, this detailed description should not be construed to unduly limit the present invention as modifications and variations in the embodiments discussed herein can be made by those of ordinary skill in the art without departing from the spirit or scope of the present inventive discovery.

The contents of each of the references cited herein, including the contents of the references cited within these primary references, are herein incorporated by reference in their entirety.

a. Definitions

The following definitions are provided in order to aid the reader in understanding the detailed description of the present invention:

"Alkyl," "alkenyl," and "alkynyl" unless otherwise noted are each straight chain or branched chain hydrocarbons of from one to about 20 carbon atoms for alkyl or to about twenty carbon atoms for alkenyl and alkynyl. The terms therefore mean, for example, methyl, ethyl, propyl, butyl, pentyl, or hexyl; ethenyl, propenyl, butenyl, pentenyl, or hexenyl; and ethynyl, propynyl, butynyl, pentynyl, or hexynyl respectively and isomers thereof.

"Aryl" means a fully unsaturated mono- or multi- ring carbocycle, including but not limited to substituted or unsubstituted phenyl, naphthyl, or anthracenyl.

"Heterocycle" means a saturated or unsaturated mono- or multi-ring carbocycle wherein one or more carbon atoms can be replaced by N, S, P, or O. This includes, for example, the following structures:

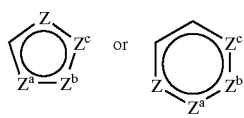

wherein one or more of Z, $Z^a$, $Z^b$, or $Z^c$ is independently C, S, P, or N, with the proviso that one of Z, $Z^a$, $Z^b$, or $Z^c$ is other than carbon, but is not O or S when attached to another Z atom by a double bond or when attached to another O or S atom. Furthermore, the optional substituents are understood to be attached Z, $Z^a$, $Z^b$, or $Z^c$ only when the atom to which the optional substituent is attached is C.

"Heteroaryl" means a fully unsaturated heterocycle.

In either "heterocycle" or "heteroaryl" the point of attachment to the molecule of interest can be at the heteroatom or elsewhere within the ring.

"Cycloalkyl" means a mono- or multi-ringed carbocycle wherein each ring contains three to about ten carbon atoms, and wherein any ring can contain one or more double or triple bonds.

The term "halogen or " "halo" means a fluoro, chloro, bromo or iodo group.

The term "haloalkyl" means alkyl substituted with one or more halogens.

The term "diyl" means a diradical moiety wherein the moiety has two points of attachment to a molecule of interest.

The term "heterocycloalkylalkyl" means an alkyl radical that is substituted with one or more heterocycle groups. Preferable heterocycloalkylalkyl radicals are "lower heterocycloalkylalkyl" radicals having one or more heterocycle groups attached to an alkyl radical having one to ten carbon atoms.

When used in combination, for example "alkylaryl" or "arylalkyl," the individual terms listed above have the meaning indicated above.

b. Compounds

The compounds of the present invention can have at least two asymmetrical carbon atoms, and therefore included racemates and stereoisomers such as diastereomers and enantiomers, in both pure form and in admixture. Such stereoisomers can be prepared using conventional techniques, either by reacting enantiomeric starting materials, or by separating isomers of compounds of the present invention.

Isomers may include geometric isomers, for example cis isomers or trans isomers across a double bond. All such isomers are contemplated among the compounds of the present invention.

The compounds of the present invention also include their tautomers, salts, solvates, and prodrugs.

In accordance with the present invention, it has been discovered that certain novel substituted-aromatic sulfonamide hydroxamic acid compounds and/or novel substituted-aromatic sulfonamide carboxylic acid compounds are effective for inhibition of matrix Metalloproteinases ("MMPs") believed to be associated with uncontrolled or otherwise pathological breakdown of connective tissue. In particular, it has been found that these substituted-aromatic ring sulfonamide hydroxamic acid, substituted-aromatic ring sulfinamide hydroxamic acid, substituted-aromatic ring sulfenamide hydroxamic acid compounds, substituted-aromatic ring sulfonamide carboxylic acid, substituted-aromatic ring sulfinamide carboxylic acid or substituted-aromatic ring sulfenamide carboxylic acid compounds are effective for inhibition of collagenase Type III (MMP-13) and neutrophil collagenase (collagenase II, MMP-8), which are believed to be particularly destructive to tissue if present or generated in abnormal quantities or concentrations. Moreover, it has been discovered that many of these novel sulfur-nitrogen bonded compounds are selective in the inhibition of MMP-13, MMP-8, and/or other MMPs associated with diseased conditions without excessive inhibition of those collagenases essential to normal bodily function such as tissue turnover and repair or other zinc proteases. More particularly, it has been found that many of the substituted-aryl- or substituted-heteroaryl-sulfonamide hydroxamic acids of the invention are selective for MMP-13 or MMP-8 with limited or minimal effect on MMP-1.

Among its many embodiments, the present invention is directed to a matrix metalloproteinase inhibiting compound having the structure of Formula VII:

Formula VII

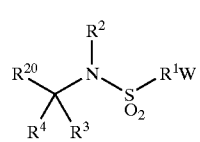

wherein:

W is independently selected from the group consisting of $-NR^5COR^6$, $-NR^5S(O)_zR^7$ where z is zero, 1, or 2, $-NR^5COOR^8$, $-NR^5CONR^8R^9$ and $-NR^{11}R^{12}$.

$R^1$ is a hydrocarbyl diyl moiety or a substituted hydrocarbyl diyl moiety. $R^1$ can be aromatic, for example 1,2-phenylene, 1,3-phenylene, 1,4-phenylene, naphthalene-1,4-diyl, or naphthalene-1,5-diyl. Alternatively, $R^1$ can be aliphatic, for example methylene, ethane-1,2-diyl, propane-1,2-diyl, or propane-1,3-diyl. $R^1$ can be a straight-chain hydrocarbyl diyl moiety, or it can be branched. For example, $R^1$ can be 2-methylpropane-1,3-diyl. Furthermore, $R^1$ can contain one or more unsaturations. For example, $R^1$ can be prop-1-ene-1,3-diyl or a cycloalkylene such as anti-1,4-cyclohexane diyl. $R^1$ can also contain a heteroatom (e.g., O, N, or S). For example, $R^1$ can be a heteroarylene such as pyridine-2,5-diyl or $R^1$ can be an aliphatic heterocycle such as morpholine-1,3-diyl. Where $R^1$ contains a heteroatom, the point of attachment of $R^1$ to the molecule can be at a heteroatom of $R^1$ or it can be at a carbon atom of $R^1$.

$R^2$ is selected from the group consisting of H, alkyl, alkenyl, alkynyl, cycloalkyl, haloalkyl, alkylaryl, arylalkyl, alkoxyalkyl, hydroxyalkyl, aminoalkyl, alkylaminoalkyl, heterocycloalkyl, heterocycloalkylalkyl aralkyl, heteroarylalkyl, cycloalkylalkyl, heterocycloalkylalkyl, alkoxyalkyl, alkylthioalkyl, hydroxycarbonylalkyl, alkylcycloalkyl, heterocycloalkylalkyl, aroylalkyl, and heteroaroylalkyl group, $-(CH_2)_x-NR^{11}R^{12}$, or $-(CH_2)_x-C(O)NR^{11}R^{12}$, wherein x is an integer from zero to 6.

$R^3$ and $R^4$ are independently selected from the group consisting of H, alkyl, alkenyl, alkynyl, cycloalkyl, haloalkyl, alkylaryl, arylalkyl, alkoxy, alkoxyalkyl, hydroxyalkyl, aminoalkyl, alkylaminoalkyl, and heterocycloalkyl, aryl, aralkyl, thioalkyl, heteroaralkyl, heteroaryl, alkoxyalkoxyalkyl, trifluoromethylalkyl, alkoxycarbonylalkyl, aralkoxycarbonylalkyl, hydroxycarbonylalkyl, alkoxyalkyl, heterocycloalkylalkyl, aryloxyalkyl, alkylthioalkyl, arylthioalkyl, heteroarylthioalkyl group, or a sulfoxide or sulfone of any of said thio-containing groups, a $-(CH_2)_x-C(O)NR^{11}R^{12}$ group, wherein x is an integer from zero to 6, and a $-(CH_2)_y-W$ group, wherein y is an integer from 1 to 6 and W is defined above. Preferably, $R^4$ is H or a $C_1$ to about $C_{12}$ alkyl group. more preferably, $R^4$ is H or a $C_1$ to about $C_4$ alkyl group. Still more preferably $R^4$ is H.

$R^2$ and $R^3$ together with the atom chain to which they are attached can optionally form a ring comprising about 3 to about 8 members.

$R^4$ is selected from the group consisting of H and $C_1$ to about $C_{20}$ alkyl group.

$R^5$ is selected from the group consisting of H and $C_1$ to about $C_{20}$ alkyl group.

$R^6$ is selected from the group consisting of H, cycloalkyl, heterocycloalkyl, aryl, heteroaryl, arylalkyl, alkylaryl, heteroaralkyl, cycloalkylalkyl, heterocycloalkylalkyl, alkoxyalkyl, alkylthioalkyl group, and a —$(CH_2)_x$—$NR^{11}R^{12}$ group wherein x is an integer from zero to about 6. The aryl or heteroaryl groups of $R^6$ are optionally substituted (unsubstituted or substituted) with one or more substituents independently selected from the group consisting of a halogen, $C_1$ to about $C_{20}$ alkyl, $C_1$ to about $C_{20}$ alkenyl, $C_1$ to about $C_{20}$ alkynyl, $C_1$ to about $C_{20}$ alkoxy, nitro, cyano, hydroxy, carboxy, hydroxycarbonylalkyl, —$(CH_2)_x$—$NR^{11}R^{12}$, wherein x is an number from zero to about 6, trifluoromethyl, alkoxycarbonyl, aminocarbonyl, thio, alkylsulfonyl, carbonylamino, aminosulfonyl, alkylsulfonamino, alkoxyalkyl, cycolalkyloxy, alkylthioalkyl or alkylthio.

Optionally, $R^5$ and $R^6$ together with the atom chain to which they are bonded can form an about 5- to about 7-membered a cyclic amide or imide that is substituted or unsubstituted.

Also optionally, $R^5$ and $R^7$ together with the atom chain to which they are bonded can form an about 5- to about 7-membered a cyclic sulfonamide that is substituted or unsubstituted.

$R^7$ is selected from the group consisting of $R^6$ and alkyl;

$R^8$ and $R^9$ are independently selected from the group consisting of $R^6$ and alkyl, or $R^8$ and $R^9$ together with the nitrogen atom to which they are attached form an about 5- to about 7-membered ring containing zero or one heteroatom that is oxygen, nitrogen or sulfur;

$R^{11}$ and $R^{12}$ are independently selected from the group consisting of H, alkyl, aryl, aralkyl, heteroaryl, heteroaralkyl, cycloalkyl, alkanoyl, aralkanoyl, and heteroaralkanoyl group, or $R^{11}$ and $R^{12}$ taken together form an about 5- to about 8-membered heterocyclo or heteroaryl ring; and $R^{13}$ is selected from the group consisting of H or $C_1$ to about $C_6$ alkyl group.

$R^{20}$ is selected from the group consisting of —C(O)OH, —C(O)NHOH, —SH, and —C(O)SH.

Preferably, the compound of the present invention has a structure of Formula VIII:

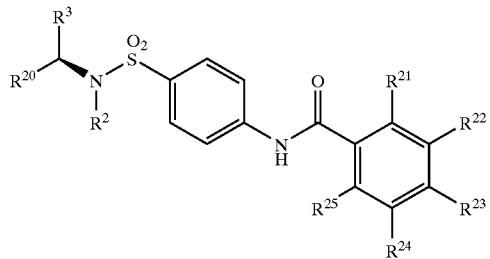

Formula VIII or a salt, an enantiomer, a diastereomer, a racemate, or a tautomer thereof, wherein:

$R^2$ is selected from the group consisting of H, alkyl, alkenyl, alkynyl, cycloalkyl, haloalkyl, alkylaryl, arylalkyl, alkoxyalkyl, hydroxyalkyl, aminoalkyl, alkylaminoalkyl, heterocycloalkyl, and heterocyloalkylalkyl;

$R^3$ is selected from the group consisting of H, alkyl, alkenyl, alkynyl, cycloalkyl, haloalkyl, alkylaryl, arylalkyl, alkoxy, alkoxyalkyl, hydroxyalkyl, aminoalkyl, alkylaminoalkyl, haloalkoxy, haloalkylthio, and heterocycloalkyl;

$R^{20}$ is selected from the group consisting of —C(O)OH, —C(O)NHOH, —SH, and —C(O)SH; and $R^{21}$, $R^{22}$, $R^{23}$, $R^{24}$, and $R^{25}$ are independently selected from the group consisting of H, $C_1$ to about $C_{20}$ alkyl, $C_1$ to about $C_{20}$ alkenyl, $C_1$ to about $C_{20}$ alkynyl, cycloalkyl, haloalkyl, alkoxyalkyl, hydroxyalkyl, aminoalkyl, alkylaminoalkyl, nitroalkyl, heterocycloalkyl, alkoxy, cycloalkoxy, alkoxycarbonyl, alkoxyalkyl, haloalkoxy, haloalkylthio, alkylamino, and carboxyalkyl.

Also, $R^2$ can be selected from the group consisting of any of the N-bonded substituent groups of the following bases: 4-acetyl cytidine; 5-(carboxyhydroxylmethyl)uridine; 2-O-methylpseudouridine; beta,D-galactosylquiosine; 2'-O-methylguanosine; inosine; N6-isopentenyladenosine; 1-methyladenosine; 1-methylpseudouridine; 1-methylguanosine; 1-methylinosine; 2,2-dimethylguanosine; 2-methyladenosine; 2-methylguanosine; 3-methylcytidine; 5-methylcytidine; N6-methyladenosine; 7-methylguanosine; 5-methoxyaminomethyl-2-thiouridine; beta, D-mannosylqueosine; 5-methoxycarbonylmethyluridine; 5-methoxyuridine; 2-methylthio-N6-isopentenyladenosine; N-((9-beta-D-ribofuranosyl-2-methylthiopurine-6-yl) carbamoyl)threonine; N-((9-beta-D-ribofuranolylpurine-6-yl)N-methyl-carbamoyl)threonine; uridine-5-oxyacetic methyl ester; uridine-5-oxyacetic acid (v); wybutoxosine; pseudouridine; queosine; 2-thiocytidine; 5-methyl-2-thiouridine; 2-thiouridine; 4-thiouridine; 5-methyluridine; N-((9-beta-D-ribofuranosylpurine-6-yl)carbamoyl) threonine; 2'-O-methyl-5-methyluridine; 2'-O-methyluridine; wybutosine; and 3-(3-amino-3-carboxypropyl)uridine, (acp3)u.

Further, $R^2$ can be selected from the group consisting of any of the side chains of the following amino acids: 2-aminoadipic acid; 3-aminoadipic acid; beta-alanine, beta-aminopropionic acid; 2-aminobutyric acid; 4-aminobutyric acid, piperidinic acid; 6-aminocaproic acid; 2-aminoheptanoic acid; 2-aminoisobutyric acid; 3-aminopimelic acid; 2,4-diaminobutyric acid; desmosine; 2,2'-diaminpimelic acid; 2,3-diaminopripionic acid; N-ethylglycihe; N-ethylasparagine; hydroxylysine; allo-hydroxylysine; isodesmosine; allo-isoleucine; N-methylglycine, sarcosine; N-methylisoleucine; N-methylvaline; norvaline; norleucine; and ornithine.

Preferably, $R^{20}$ of Formula VIII is selected from the group consisting of —C(O)OH and —C(O)NHOH. Preferably $R^{21}$ and $R^{25}$ of Formula VIII are both H. More preferably, $R^{21}$, $R^{22}$, $R^{24}$, and $R^{25}$ are H. When $R^{21}$, $R^{22}$, $R^{24}$, and $R^{25}$ are H, preferably $R^{23}$ is $C_1$ to about $C_{20}$ alkyl and more preferably $R^{23}$ is $C_1$ to about $C_{20}$ linear alkyl. When $R^{20}$ of Formula VIII is —C(O)OH, $R^3$ is preferably selected from the group consisting of alkyl, alkenyl, alkynyl, haloalkoxy, haloalkylthio, and heterocycloalkyl; more preferably $R^3$ is heterocycloalkyl, and more preferably still $R^3$ is 2-(N-morpholino)ethyl. When $R^{20}$ of Formula VIII is —C(O)NHOH, $R^3$ is preferably selected from the group consisting of alkyl, alkenyl, alkynyl, haloalkoxy, haloalkylthio, and heterocycloalkyl; more preferably $R^3$ is heterocycloalkyl, and more preferably still $R^3$ is 2-(N-morpholino)ethyl.

Table I below shows preferred compounds of the present invention. The represented compounds are meant to include their salts, enantiomers, diastereomers, racemates, and tautomers.

TABLE I

| Formula Number | Structure |
|---|---|
| IX | 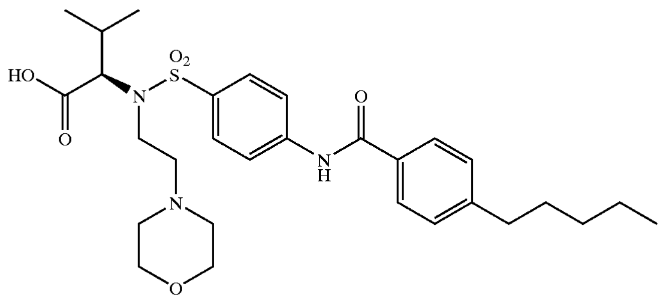 |
| X | 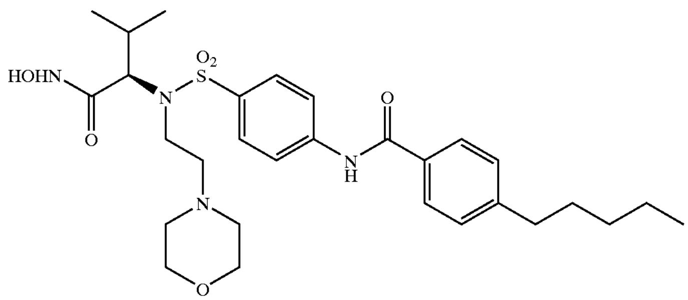 |
| XI | 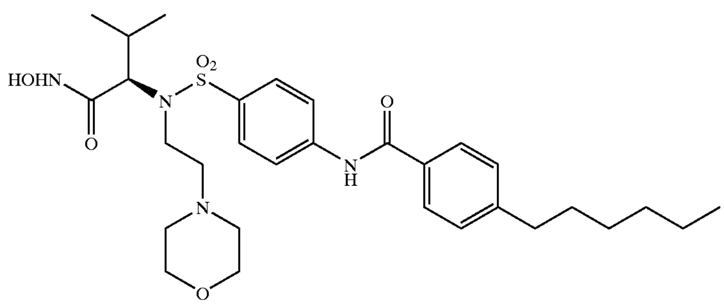 |
| XII | 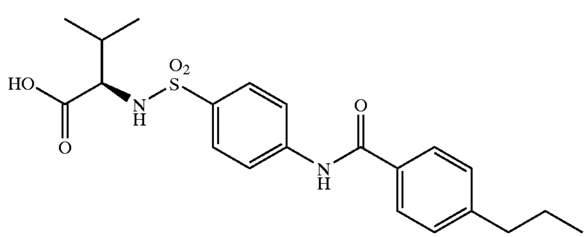 |

Without being bound to a particular mechanism, it is believed that some of the compounds of the present invention provide selective inhibition of certain MMPs, particularly MMP-8 or MMP-13, in part by causing a change in the conformation of the amino acid residue backbone of the inhibited MMP.

The present invention is further directed to a method of changing the conformation of a matrix metalloproteinase wherein the method comprises contacting the matrix metalloproteinase with a compound having the structure of Formula XIII:

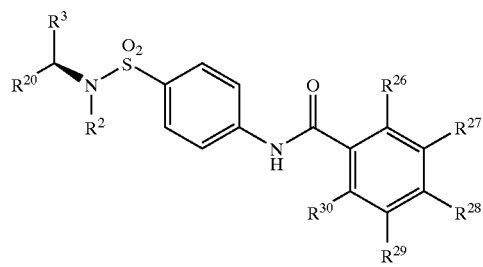

Figure XIII or a salt, an enantiomer, a diastereomer, a racemate, or a tautomer thereof, thereby changing the conformation of the matrix metalloproteinase, wherein:

$R^2$ is selected from the group consisting of H, alkyl, alkenyl, alkynyl, cycloalkyl, haloalkyl, alkylaryl, arylalkyl, alkoxyalkyl, hydroxyalkyl, aminoalkyl, alkylaminoalkyl, heterocycloalkyl, and heterocycloalkylalkyl;

$R^3$ is selected from the group consisting of H, alkyl, alkenyl, alkynyl, cycloalkyl, haloalkyl, alkylaryl, arylalkyl, alkoxy, alkoxyalkyl, hydroxyalkyl, aminoalkyl, alkylaminoalkyl, and heterocycloalkyl;

$R^{20}$ is selected from the group consisting of —C(O)OH, —C(O)NHOH, —SH, and —C(O)SH; and $R^{26}$, $R^{27}$, $R^{28}$, $R^{29}$, and $R^{30}$ are independently selected from the group consisting of about $C_3$ to about $C_{20}$ alkyl, about $C_3$ to about $C_{20}$ alkenyl, about $C_3$ to about $C_{20}$ alkynyl, cycloalkyl, haloalkyl, alkoxyalkyl, hydroxyalkyl, aminoalkyl, alkylaminoalkyl, nitroalkyl, heterocycloalkyl, and carboxyalkyl.

Preferably for the method of changing the conformation of an MMP, $R^{20}$ of Formula XIII is selected from the group consisting of —C(O)OH and —C(O)NHOH. $R^3$ is preferably a $C_1$ to about $C_{12}$ alkyl, more preferably $R^3$ is a $C_1$ to about $C_4$ alkyl, and more preferably still $R^3$ is isopropyl. $R^2$ is preferably heterocycloalkylalkyl and more preferably $R^2$ is 2-(N-morpholino)ethyl. Preferably $R^{26}$ and $R^{30}$ are H. More preferably, $R^{26}$, $R^{27}$, $R^{29}$, and $R^{30}$ are H. $R^{28}$ can be an alkyl group of any convenient size. When $R^{26}$, $R^{27}$, $R^{29}$, and $R^{30}$ are H, $R^{28}$ is preferably about $C_3$ to about $C_{20}$ alkyl and more preferably $R^{28}$ is about $C_3$ to about $C_{20}$ linear alkyl. More preferably still $R^{28}$ is n-propyl, n-butyl, n-pentyl or n-hexyl. Compounds IX, X, XI, and XII of Table I (or a salt, an enantiomer, a diastereomer, a racemate, or a tautomer thereof) each is useful in the present invention.

Surprisingly, the compounds of the Formula XIII are particularly useful in changing the conformation of MMP enzymes, especially MMP-8 and/or MMP-13. Crystal structures of MMP-8 complexed with MMP inhibitor compounds of Formula XIII compared with crystal structures of MMP-8 complexed with the compound of Formula XIV or the compound of Formula XV establish a three-dimensional structure-activity relationship.

Formula XIV

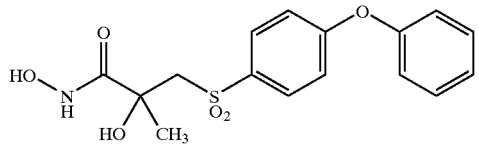

Formula XV

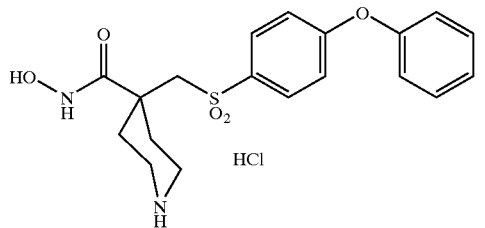

The catalytic domain (residues 85–242) of MMP-8, neutrophil collagenase, folds into a compact globular structure. It has an approximate diameter of 30 Å. The inhibitors interact with the protein through chelation of the catalytic zinc ion, hydrogen bonding with the backbone —NH— of Leu 160, and hydrophobic interactions in the nonpolar S1' pocket. In MMP-8, the S1' pocket is formed from residues 193–197 that form a turn of a longer helix and residues 214–229 of a loop region. The S1' pocket in MMP-8 is not as deep as in some other MMPs (e.g., stromelysin). The conformation of the S1' pocket changes as the P1' substituent on the inhibitor is made progressively longer.

X-ray crystallographic techniques described herein showed the co-extensive reach of the P1' arms of the inhibitors XII, IX, X, and XI, except that as the alkyl group of the 4-alkylbenzamide moiety increases in length, the steric requirements of each inhibitor also increases. The P1' arm of each inhibitor fits into the MMP-8 S1' pocket. In order to accommodate an increase in the steric requirement of the P1' arm, the amino acid residues of the S1' pocket must change their conformations.

FIG. 2 shows MMP-8 S1' amino acid backbone residues which reside within 5 Å of a complexed inhibitor molecule as determined by the X-ray crystallographic techniques described herein. A blank in FIG. 3 indicates that the residue lies within 5 Å of the inhibitor whereas the word "no" indicates that the residue lies further than 5 Å from the complexed inhibitor.

Figure 4:
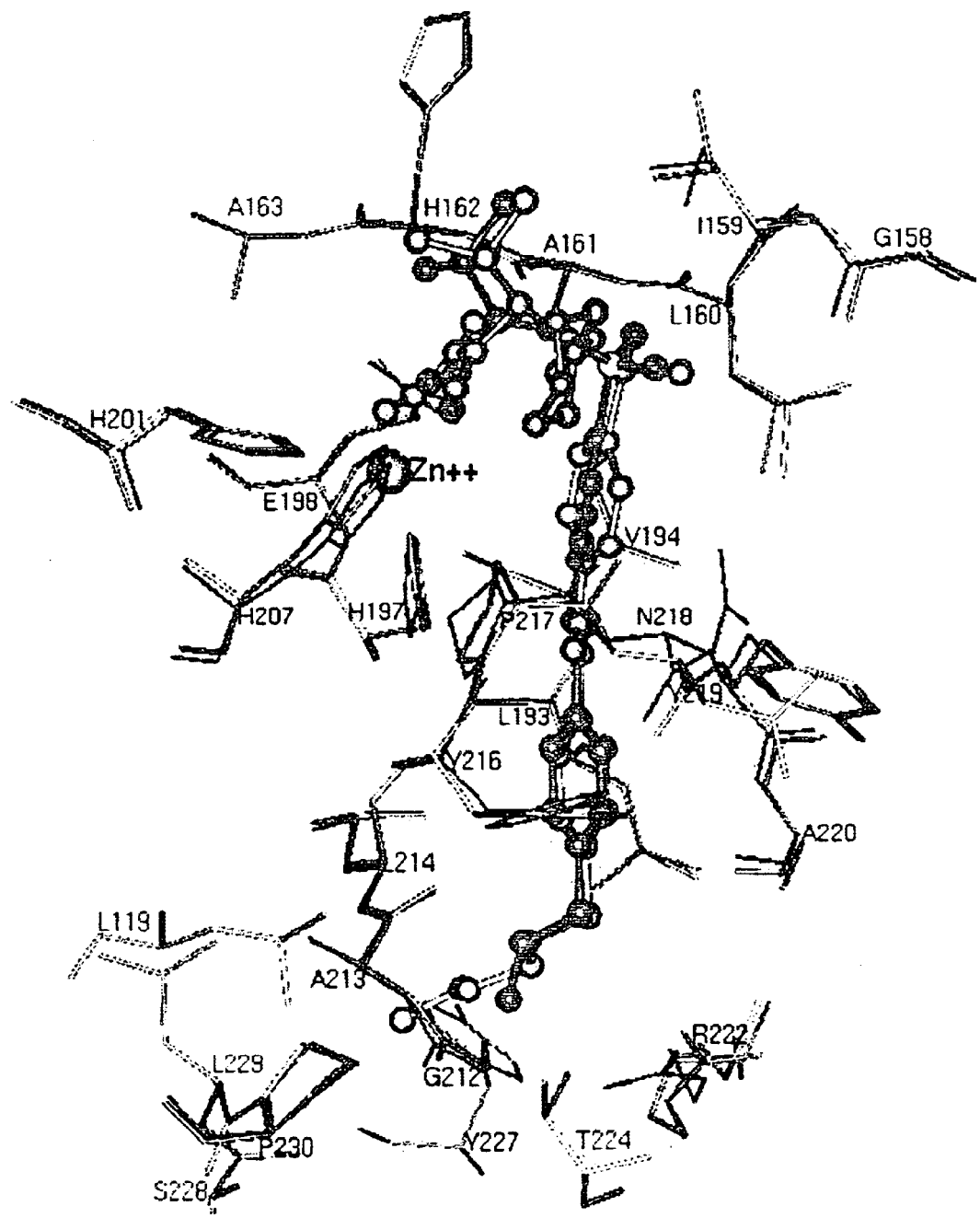

FIG. 4 shows a comparison of the S1' pockets of MMP-1 and of MMP-8.

FIGS. 5, 6, 7, and 8 show the effect of progressively lengthening the P1' group of the MMP inhibitor on the conformation of the substituents on amino acid residues of the S1' pocket.

X-ray crystallography of the complex of the compound of Formula XII or the compound of Formula XIV with MMP-8 showed that the P1' group (including the 4-propylbenzamide moiety) of compound XII sterically interferes with the side chain of the Arg 222 (R222)residue of the S1' pocket of MMP-8, while the P1' group of composed XIV is much shorter and does not sterically interfere with the Arg 222 the side chain. Complexed compound XII causes the Arg 222 the side chain to move out of the way of the large P1' group of XII.

FIG. 3 shows a comparison of the X-ray crystallographic conformation of amino acid residues in the S1' pocket of MMP-8 when either the compound of Formula XII (black) or the compound of Formula IX (grey) is complexed with MMP-8. The P1' group of compound IX (including the 4-pentylbenzamide moiety) is larger still than the P1' group of compound XII. Because of increased steric interference, the IX P1' group of compound IX causes the side chain of the Arg 222 (R222)residue of the S1' pocket of MMP-8 to move even further away from the pocket than does the P1' compound group of XII.

The P1' group of X (including the 4-hexylbenzamide moiety) is larger still than the P1' group of XII. X-ray crystallography showed that, due to increased steric interference, the P1' group of compound X causes the side chain of the Arg 222 (R222)residue of the S1' pocket of MMP-8 to move as far or further away from the pocket than does the XII P1' group.

FIG. 4 shows a comparison of the X-ray crystallographic conformation of amino acid residues in the S1' pocket of MMP-8 when either the compound of Formula XII (black) or the compound of Formula XI (grey) is complexed with MMP-8. This Figure shows a result similar to the comparison between compounds XII and X.

FIGS. 9, 10, 11, and 12 show the effect of progressively lengthening the P1' group of the MMP inhibitor on the conformation of the backbone of the S1' pocket.

X-ray crystallography if the amino acid backbone of the S1' pocket of MMP-8 when either the compound of Formula XII or the compound of Formula XIV is complexed with MMP-8 showed that compound XII affects the conformation of the side chain of the Arg 222 (R222) residue of the S1' pocket relative to compound XIV. It also showed that each compound has essentially no effect on the conformation of the amino acid backbone. Tyr 227 (Y227) shows little change when either compound XII or XIV is complexed in the S1' pocket.

X-ray crystallography of the amino acid backbone of the S1' pocket of MMP-8 when either the compound of Formula XII or the compound of Formula X is completed with MMP-8 showed that the longer 4-pentylbenzamide moiety of compound X causes the backbone to deform significantly relative to the case in which compound XII is complexed. In addition, compound X causes the Arg 222 and Tyr 227 side chains to move significantly relative to the case in which compound XII is complexed.

X-ray crystallography of the amino acid backbone of the S1' pocket of MMP-8 when either the compound of Formula XII (red) or the compound of Formula IX is complexed with MMP-8 compound that the longer 4-pentylbenzamide moiety of compound IX causes the backbone to deform significantly relative to the case in which compound XII is complexed. In addition, compound IX causes the Arg 222 and Tyr 227 side chains to move significantly relative to the case in which compound XII is complexed.

X-ray crystallography of the amino acid backbone of the S1' pocket of MMP-8 when either the compound of Formula XII or the compound of Formula XI is complexed with MMP-8 showed that the longer 4-hexylbenzamide moiety of compound XI causes the backbone to deform significantly relative to the case in which compound XII is completed. In addition, XI causes the Arg 222 and Tyr 227 side chains to move significantly relative to the case in which XII is complexed.

Complexes of MMP-8 with compounds XII and XIV show similar temperature factors indicating that the MMP-8 backbone has similar thermal motion in both cases. However, MMP-8 complexes with compounds XI, X, and IX cause a progressive increase in the temperature factor in residues 221–230, indicating that they are causing greater thermal motion in that region of the S1' pocket of MMP-8 relative to compounds X or XIV.

FIG. 5 shows the ($\phi,\psi$) distribution among the amino acid residues of MMP-8 from 222 to 231.

Comparison between the electrostatic surfaces of the MMP-8 complex with compounds XIV and XI showed shows that compound XI has caused a change in the conformation of MMP-8 relative to compouond XIV as evidenced by the opening created by compound XI in the S1' pocket caused by the change in conformation of the amino acid residue backbone of MMP-8. This opening is absent from the compound XIV-MMP-8 complex. The electrostatic surfaces were calculated using the GRASP program (A. Nicholls et al., "Protein folding and association: Insights from the interfacial and thermodynamic properties of hydrocarbons,"*Protein Str. Funct. Gen.* 11, 281–296 (1991)).

Stepwise changes of the MMP-8 protein are observed in progressing from complexes of MMP-8 with XIV, XII, IX, X, and XI. The S1' it pocket becomes deeper, first by the movement of amino acid residue side chains (especially Arg 222 and Tyr 227), then by a movement of the backbone in the 224–228 region.

The present invention is also directed to a method of inhibiting a matrix metalloproteinase wherein the method comprises contacting the matrix metalloproteinase with a compound of Formula VIII (for which each of the substituents are as defined above) thereby inhibiting the matrix metalloproteinase. Preferably for the method of inhibiting an MMP, $R^{20}$ of Formula XIII is selected from the group consisting of —C(O)OH and —C(O)NHOH. $R^3$ is preferably a $C_1$ to about $C_{12}$ alkyl, more preferably $R^3$ is a $C_1$ to about $C_4$ alkyl, and more preferably still $R^3$ is isopropyl. $R^2$ is preferably heterocycloalkylalkyl and more preferably $R^2$ is 2-(N-morpholino)ethyl. Preferably $R^{21}$ and $R^{25}$ of Formula VIII are both H. More preferably, $R^{21}$, $R^{22}$, $R^{24}$, and $R^{25}$ are H. $R^{23}$ can be an alkyl group of any convenient size. When $R^{21}$, $R^{22}$, $R^{24}$, and $R^{25}$ are H, preferably $R^{23}$ is $C_1$ to about $C_{20}$ alkyl and more preferably $R^{23}$ is $C_1$ to about $C_{20}$ linear alkyl. Compounds IX, X, XI, and XII of Table I (or a salt, an enantiomer, a diastereomer, a racemate, or a tautomer thereof) each is useful in the present invention. The compounds of the present invention are particularly useful in inhibiting MMP-8 and/or MMP-13.

Another embodiment of the present invention is directed toward a method for the treatment of osteoarthritis in a mammal wherein the method comprises providing to the mammal an osteoarthritis-treating-effective amount of a compound of Formula VIII (for which each of the substituents are as defined above). The mammal can be, for example, a human. Each of the compounds shown in Table I will be useful in the treatment of a human for osteoarthritis. Alternatively, the method for treating osteoarthritis can be directed to a veterinary subject, for example a cat or a dog.

c. Compound Syntheses

The starting materials for use in the preparation of the compounds of the present invention are known or can be prepared by conventional methods known to a skilled person or in an analogous manned to processes described in the art.

Generally, the compounds of the present invention can be prepared by methods described in detail in U.S. patent application Ser. No. 09/230,205, herein incorporated by reference.

Schemes I and III and Schemes 1, 2, 4, 5, 6, and 7 illustrate procedures with examples of chemical transformations that may be useful for the preparation of compounds of this invention. These syntheses, as with all of the reactions discussed herein, can be carried out under a dry inert atmosphere such a nitrogen or argon if desired. Selected reactions known to those skilled in the art, can be carried out under a dry atmosphere such as dry air whereas other synthetic steps, for example, aqueous acid or base ester or amide hydrolyses, can be carried out under laboratory air.

Thus, in general, the choices of starting material and reaction conditions can vary as is well know to those skilled in the art. Usually, no single set of conditions is limiting since variations can be applied as required. Conditions will also will be selected as desired to suit a specific purpose such as small scale preparations or large scale preparations. In either case, the use of less safe or less environmentally sound materials or reagents will usually be minimized. Examples of such less desirable materials are diazomethane, diethyl ether, heavy metal salts, dimethyl sulfide, chloroform, benzene and the like.

Scheme 1

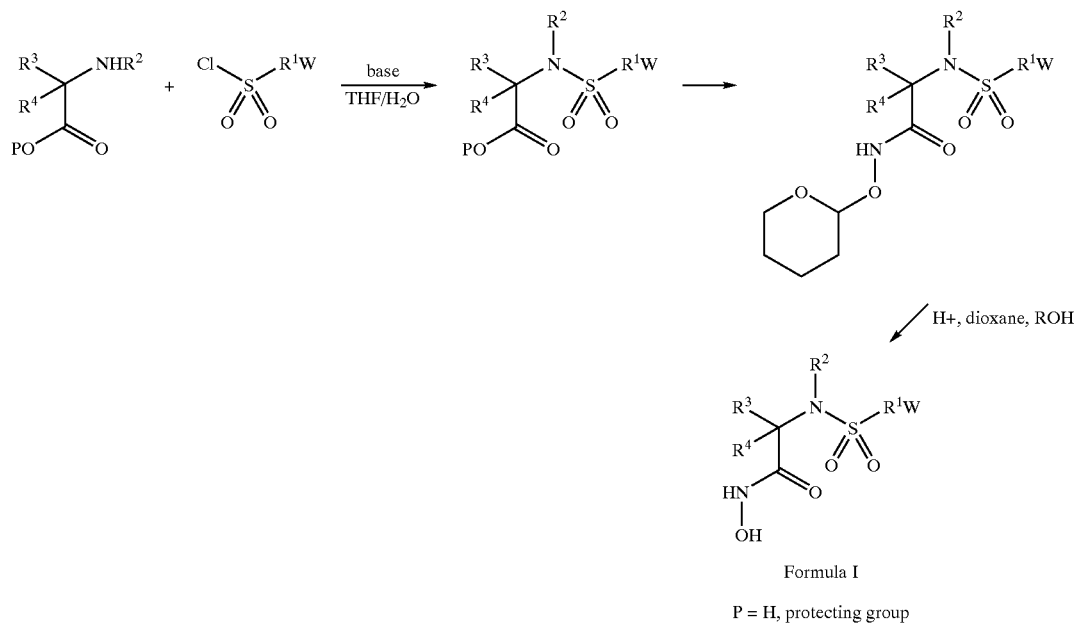

Formula I

P = H, protecting group

Scheme I shows the conversion of an N-substituted alpha-amino acid, protected or unprotected, into a compound of Formula I. The amino acid may be protected with a group P such as an alkyl ester such as methyl, ethyl, tert-butyl, tetrahydropyranyl and the like or arylalkyl ester such as benzyl. Treatment of this amine with a sulfonyl, sulfinyl or sulfenyl chloride would provide the corresponding amide. A base would normally be used to inactivate the HCl released from the acid chloride and it would be such that it would not react with the sulfonyl chloride, i.e., ammonia, primary or secondary amines would not normally be used. Examples of bases that can be used include, for example, metal hydroxides such as sodium, potassium, lithium or magnesium hydroxide, oxides such as those of sodium, potassium, lithium, calcium or magnesium, metal carbonates such as those of sodium, potassium, lithium, calcium or magnesium, metal bicarbonates such as sodium bicarbonate or potassium bicarbonate, primary, secondary or tertiary organic amines such as alkyl amines, arylalkyl amines, alkylarylalkyl amines, heterocyclic amines or heteroaryl amines, ammonium hydroxides or quaternary ammonium hydroxides. As non-limiting examples, such amines can include triethyl amine, trimethyl amine, diisopropyl amine, methyldiisopropyl amine, diazabicyclononane, tribenzyl amine, dimethylbenzyl amine, morpholine, N-methylmorpholine, N,N'-dimethylpiperazine, N-ethylpiperidine, 1,1,5,5-tetramethylpiperidine, dimethylaminopyridine, pyridine, quinoline, tetramethylethylenediamine and the like. Non-limiting examples of ammonium hydroxides, usually made from amines and water, can include ammonium hydroxide, triethyl ammonium hydroxide, trimethyl ammonium hydroxide, methyldiiospropyl ammonium hydroxide, tribenzyl ammonium hydroxide, dimethylbenzyl ammonium hydroxide, morpholinium hydroxide, N-methylmorpholinium hydroxide, N,N'-dimethylpiperazinium hydroxide, N-ethylpiperidinium hydroxide, and the like. As non-limiting examples, quaternary ammonium hydroxides can include tetraethyl ammonium hydroxide, tetramethyl ammonium hydroxide, dimethyldiiospropyl ammonium hydroxide, benzymethyldiisopropyl ammonium hydroxide, methyldiazabicyclononyl ammonium hydroxide, methyltribenzyl ammonium hydroxide, N,N-dimethylmorpholinium hydroxide, N,N,N',N'-tetramethylpiperazenium hydroxide, and N-ethyl-N'-hexylpiperidinium hydroxide and the like. Metal hydrides, amide or alcoholates such as calcium hydride, sodium hydride, potassium hydride, lithium hydride, sodium methoxide, potassium tert-butoxide, calcium ethoxide, magnesium ethoxide, sodium amide, potassium diisopropyl amide and the like may also be suitable reagents. Organometallic deprotonating agents such as alkyl or aryl lithium reagents such as methyl, phenyl or butyl lithium, Grignard reagents such as methylmagnesium bromide or methylmagnesium chloride, organocadmium reagents such as dimethylcadmium and the like may also serve as bases for causing salt formation or catalyzing the reaction. Quaternary ammonium hydratides or mixed salts are also useful for aiding phase transfer couplings or serving as phase transfer reagents.

The first reaction in Scheme 1 also illustrated the use of a mixed solvent $THF/H_2O$. This is one solvent system however others may be useful also. For example, the reaction media can consist of a single solvent, mixed solvents of the same or different classes or serve as a reagent in a single or mixed solvent system. The solvents can be protic, non-protic or dipolar aprotic. Non-limiting examples of protic solvents include water, methanol (MeOH), denatured or pure 95% or absolute ethanol, isopropanol and the like. Typical non-protic solvents include acetone, tetrahydrofuran (THF), dioxane, diethylether (ether), tert-butylmethyl ether (TBME), aromatics such as xylene, toluene, or benzene, ethyl acetate, methyl acetate, butyl acetate, trichloroethane, methylene chloride, ethylenedichloride (EDC), hexane, heptane, isooctane, cyclohexane and the like. Dipolar aprotic solvents include compounds such as dimethylformamide (DMF), dimethylacetamide (DMAc), acetonitrile, nitromethane, tetramethylurea, N-methylpyrrolidone and the like.

Scheme 2

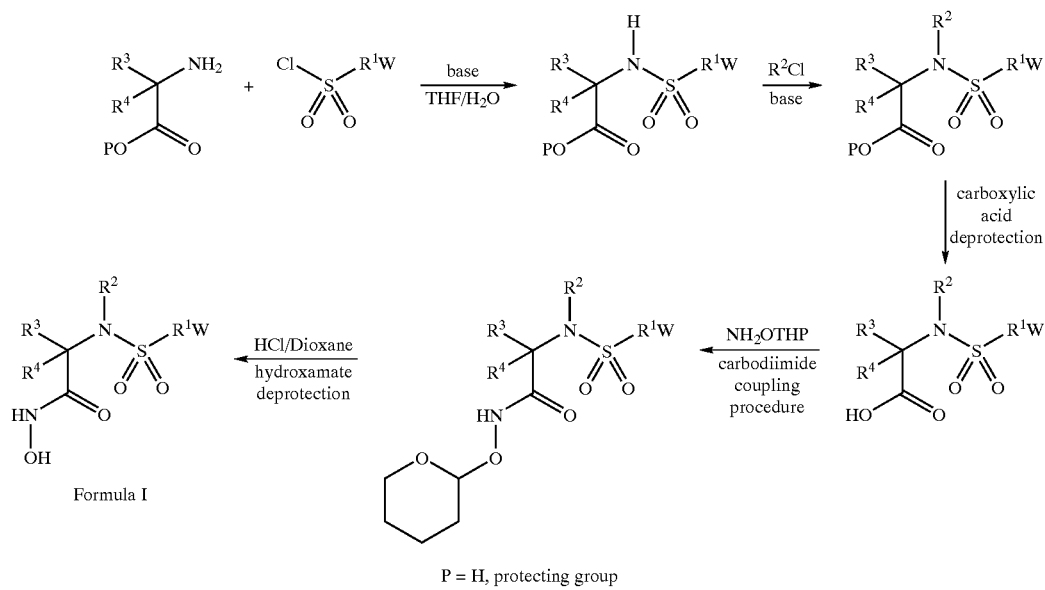

P = H, protecting group

Non-limiting examples of ammonium hydroxides, usually made from amines and water, can include ammonium hydroxide, triethyl ammonium hydroxide, trimethyl ammonium hydroxide, methyldiiospropyl ammonium hydroxide, tribenzyl ammonium hydroxide, dimethylbenzyl ammonium hydroxide, morpholinium hydroxide, N-methylmorpholinium hydroxide, N,N'dimethylpiperazinium hydroxide, N-ethylpiperidinium hydroxide, and the like. As non-limiting examples, quaternary ammonium hydroxides can include tetraethyl ammonium hydroxide, tetramethyl ammonium hydroxide, dimethyldiiospropyl ammonium hydroxide, benzymethyldiisopropyl ammonium hydroxide, methyldiazabicyclononyl ammonium hydroxide, methyltribenzyl ammonium hydroxide, N,N-dimethylmorpholinium hydroxide, N,N,N',N'-tetramethylpiperazenium hydroxide, and N-ethyl-N'-hexylpiperidinium hydroxide and the like. Metal hydrides, amide or alcoholates such as calcium hydride, sodium hydride, potassium hydride, lithium hydride, sodium methoxide, potassium tert-butoxide, calcium ethoxide, magnesium ethoxide, sodium amide, potassium diisopropyl amide and the like may also be suitable reagents. Organometallic deprotonating agents such as alkyl or aryl lithium reagents such as methyl, phenyl or butyl lithium, Grignard reagents such as methylmagnesium bromide or methylmagnesium chloride, organocadmium reagents such as dimethylcadmium and the like may also serve as bases for causing salt formation or catalyzing the reaction. Quaternary ammonium hydroxides or mixed salts are also useful for aiding phase transfer couplings or serving as phase transfer reagents.

The first reaction in Scheme 1 also illustrated the use of a mixed solvent THF/H$_2$O. This is one solvent system however others may be useful also. For example, the reaction media can consist of a single solvent, mixed solvents of the same or different classes or serve as a reagent in a single or mixed solvent system. The solvents can be protic, non-protic or dipolar aprotic. Non-limiting examples of protic solvents include water, methanol (MeOH), denatured or pure 95% or absolute ethanol, isopropanol and the like. Typical non-protic solvents include acetone, tetrahydrofurane (THF), dioxane, diethylether (ether), tert-butylmethyl ether (TBME), aromatics such as xylene, toluene, or benzene, ethyl acetate, methyl acetate, butyl acetate, trichloroethane, methylene chloride, ethylenedichloride (EDC), hexane, heptane, isooctane, cyclohexane and the like. Dipolar aprotic solvents include compounds such as dimethylformamide (DMF), dimethylacetamide (DMAc), acetonitrile, nitromethane, tetramethylurea, N-methylpyrrolidone and the like.

Non-limiting examples of reagents that can be used as solvents or as part of a mixed solvent system include organic or inorganic mono- or multi-protic acids or bases such as hydrochloric acid, phosphoric acid, sulfuric acid, acetic acid, formic acid, citric acid, succinic acid, triethylamine, morpholine, N-methylmorpholine, piperidine, pyrazine, piperazine, pyridine, potassium hydroxide, sodium hydroxide, alcohols, ammonia or amines for making esters or amides and the like.

Acids are used in many reactions during various synthesis. Scheme 1 illustrates acid use for the removal of the THP protecting group to produce the hydroxamic acid of Formula I. The acid might be mono-, di- or tri-protic organic or inorganic acids. Examples of acids include hydrochloric acid, phosphoric acid, sulfuric acid, acetic acid, formic acid, citric acid, succinic acid, hydrobromic acid, hydrofluoric acid, carbonic acid, phosphorus acid, p-toluene sulfonic acid, trifluoromethane sulfonic acid, trifluoroacetic acid, difluoroacetic acid, benzoic acid, methane sulfonic acid, benzene sulfonic acid, 2,6-dimethylbenzene sulfonic acid, trichloroacetic acid, nitrobenzoic acid, dinitrobenzoic acid, trinitrobenzoic acid, and the like. They might also be Lewis acids such as aluminum chloride, borontrifluoride, antimony pentafluoride and the like. A preferred solvent in this type reaction is dioxane eith an alcohol or water however almost any solvent system with one component being a protic solvent can be useful.

Scheme I illustrates conversion of a carboxylic acid protected as an ester or amide into an hydroxamic acid derivative such as a O-arylalkylether or O-cycloalkoxyalkylether group. In particular, the this Scheme the protecting group on the hydroxylamine is the THP group. In the case where hydroxylamine is used, treatment of an ester or amide with one or more equivalents of hydroxylamine hydrochloride at room temperature or above in a solvent or solvents, usually protic or partially protic, such as those listed above can provide a hydroxamic acid directly. This exchange process may be further catalyzed by the addition of additional acid. Alternatively, a base such as a salt of an alcohol used as a solvent, for example, sodium methoxide in methanol, can be used to form hydroxylamine from hydroxylamine hydrochloride in situ which can exchange with an ester or amide. As mentioned above, exchange can be carried out with a protected hydroxyl amine such as tetrahydropyranyl-hydroxyamine ($THPONH_2$), benzylhydroxylamine ($BnONH_2$), and the like in which case compounds such as shown in Scheme 1 that are tetrahydropyranyl (THP) or benzyl (Bn) hydroxamic acid derivatives are the products. Removal of the protecting groups when desired, for example, following further transformations in another part of the molecule or following storage, is accomplished by standard methods well known in the art such as acid hydrolysis of the THP group as discussed above or reductive removal of the benzyl group with hydrogen and a metal catalyst such as palladium, platinum, palladium on carbon or nickel.

In the case where P is hydrogen, i.e., where the intermediate is a carboxylic acid, standard coupling reactions can be used. For example, the acid can be converted into an acid chloride, mixed anhydride or activated ester and treated with hydroxylamine or a protected hydroxylamine in the presence of a non-competitive base to the nitrogen acylated compound. This is the same product as discussed above. Couplings of this nature are well known in the art and especially the art related to peptide and amino acid chemistry.

Scheme II illustrates another possible synthesis of the compounds of Formula I starting with a protected or unprotected amino acid. Sulfonylation of the amino group is accomplished as discussed above to produce the sulfonamide II-B. This compound is a secondary sulfonamide and, as such, is acidic and can be alkylated with an $R^2$ group. Alkylation, a process well known in the art, can be carried by treatment of the sulfonamide with base to form the corresponding anion, adding an electrophilic reagent and allowing the $SN_2$ reaction to proceed. Electrophiles include halogen derivatives, sulfonate esters, epoxides and the like. The bases and solvents discussed with regard to Scheme I are applicable in this Scheme. Preferred bases are those that are hindered such that competition with the electrophile is minimized. Additional preferred bases are metal hydrides, amide anions or organometallic bases such as a butyl lithium. The solvents, solvent mixtures or solvent/reagent mixtures discussed are satisfactory but non-protic or dipolar aprotic solvents such as acetone, acetonitrile, DMF and the like are examples of preferred classes.

Scheme III illustrates the potential for use of a sulfonyl chloride reagent, specifically nitrobenzenesulfonyl chloride, to prepare compounds of this invention. It should be noted that this reagent is for illustration and is not to be considered limiting or required. After coupling with an amino acid and alkylation of the coupling product if required, the nitrosulfonamide can be reduced to provide a useful amino compound. The amino group can be alkylated if desired. It can also be acylated with an aroyl chloride, heteroaryl or other $R^6$ amine carbonyl froming agent to form a —C(=O)— or —S(=O)$_n$— compound of this invention. The amino sulfonamide can also be reacted with a carbonic acid ester chloride as shown in Scheme IV, a sulfonyl chloride as shown in Scheme V or in Scheme VII or a carbamoyl chloride or isocyanate as shown in Scheme VI to produce the corresponding carbamate, sulfonamides. or ureas of this invention. Acylation of amines of this type are well known in the art and the reagents are also well known. Usually these reactions are carried out in aprotic solvents under an inert or/and dry atmosphere at about 45° C. to about 10° C. An equivalent of a non-competitive base is usually used with sulfonyl chloride, acid chloride or carbonyl chloride reagents. Following this acylation step, synthesis of the hydroxamic acid products of this invention can proceed as discussed above for Scheme I and Scheme II.

Schemes II through VI also illustrate the possible reduction of a nitrobenzenesulfonamide to produce an amino sulfonamide. The reduction of nitro groups to amines is will know in the art with a preferred method being hydrogenation. There is usually a metal catalyst such at Rh, Pd, Pt, Ni or the like with or without an additional support such as carbon, barium carbonate and the like. Solvents can be protic or non-protic pure solvents or mixed solvents as required. The reductions can be carried out at atmospheric pressure to a pressure of multiple atmospheres with atmospheric pressure to about 40 pounds per square inch (psi) preferred.

Other sulfonyl chloride reagents can also be used in the preparation of compounds of this invention as outline in the Schemes. Examples are fluoroaryl or fluoroheteroaryl sulfonyl chlorides, azidoaryl or azidoheteroaryl or amide, carbonate, carbamate or urea substituted aryl or heteroaryl sulfonyl chloride reagents. Azides, for example, can be reduced to an amino group using hydrogen with a metal catalyst or metal chelate catalyst or activated hydride transfer reagent. The fluoro substituted sulfonic acid or sulfonamide can be treated with a nucleophile such as ammonia or a primary amine, under pressure if desired, to provide an amino or substituted (R5) amino group that can then be reacted a reagent as outline in Scheme III and in Schemes 4–7 inclusive.

Scheme III

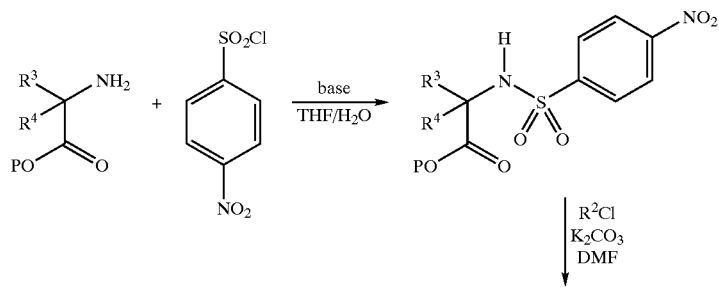

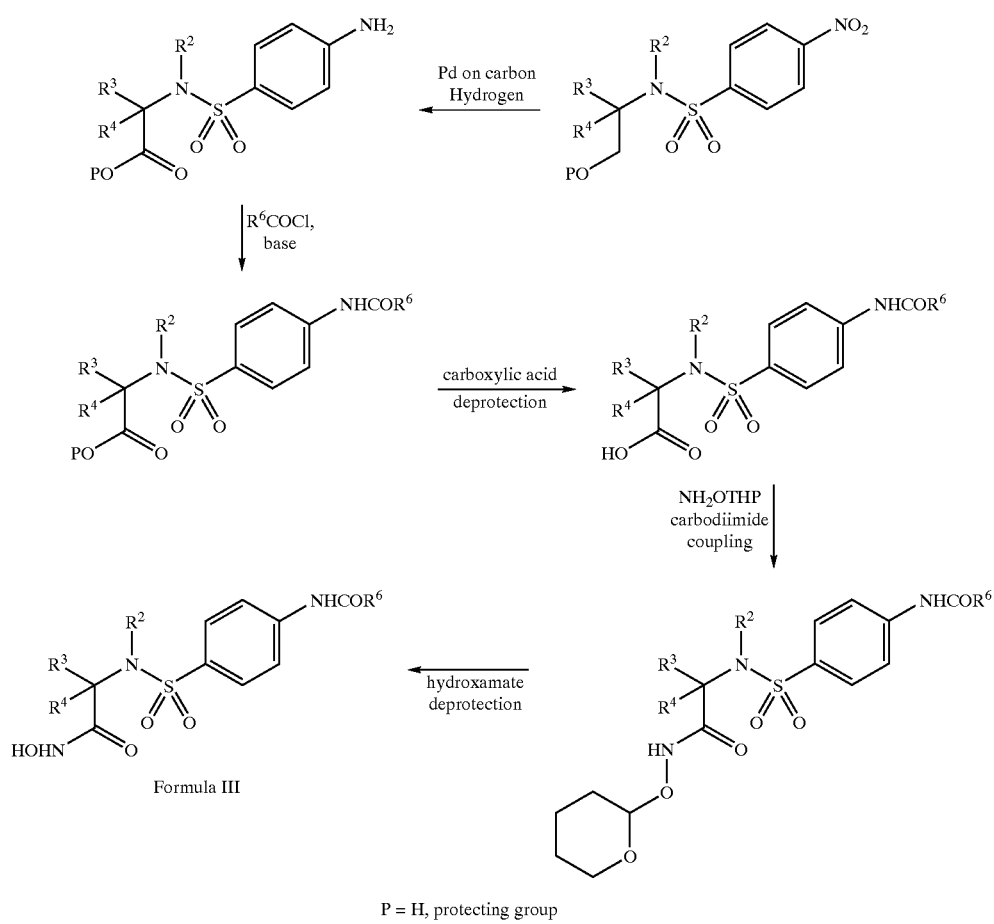
P = H, protecting group
Scheme 4
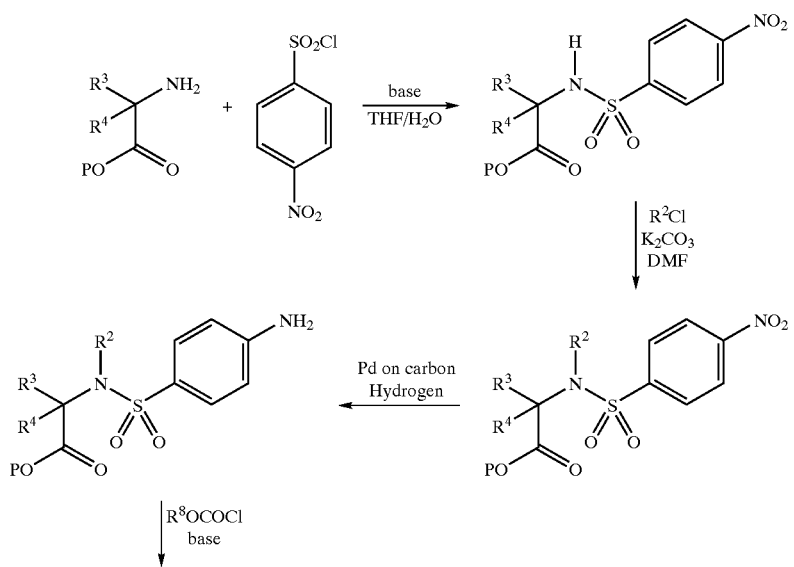

-continued
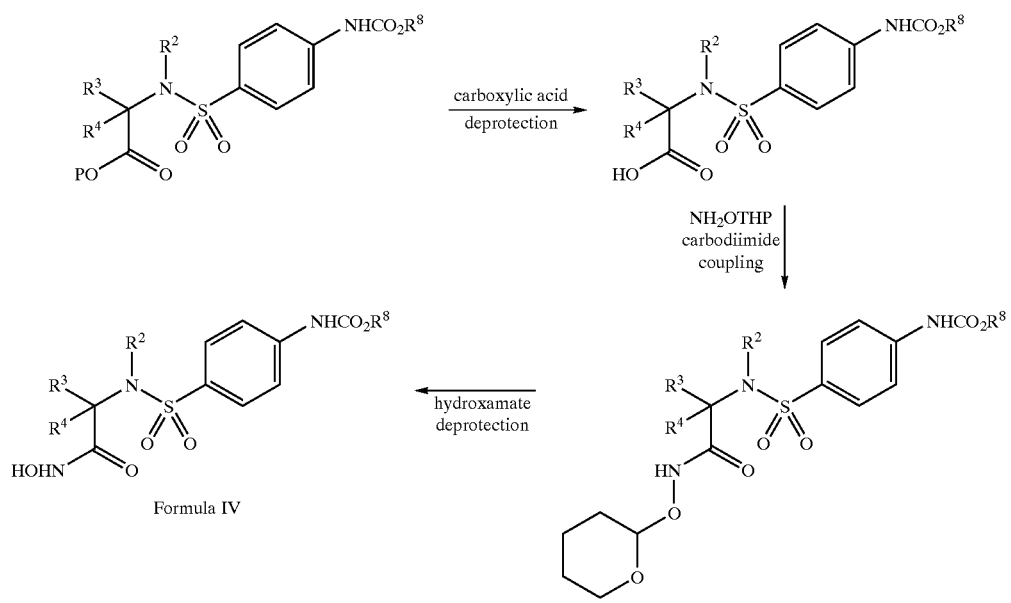
P = H, protecting group
Scheme 5
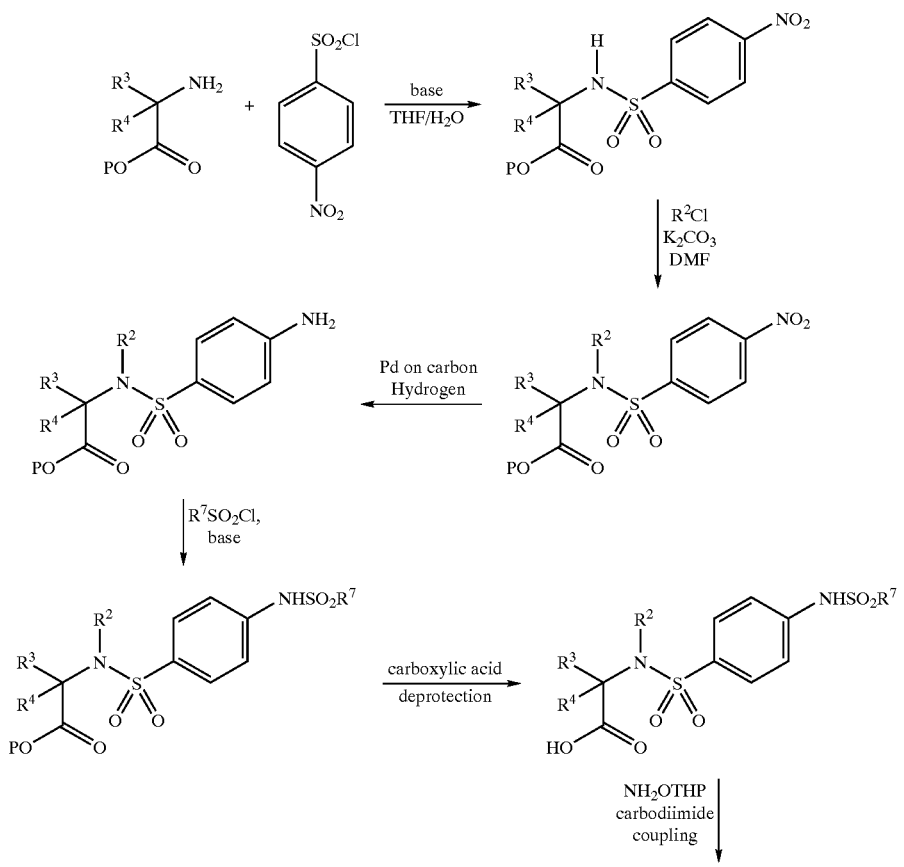

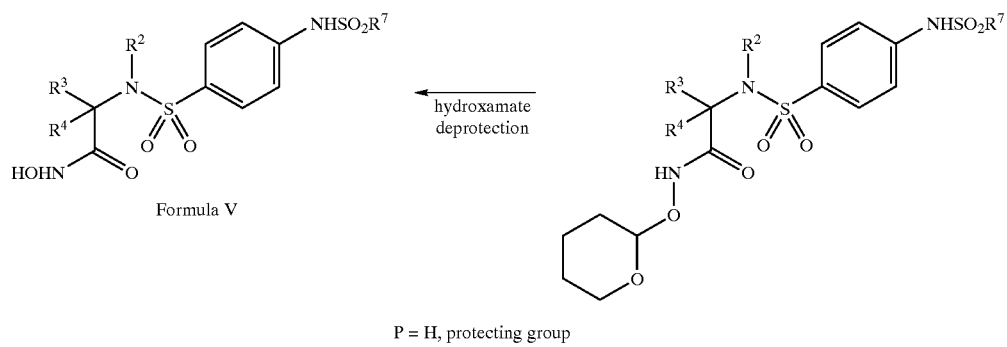
Formula V
P = H, protecting group
Scheme 6
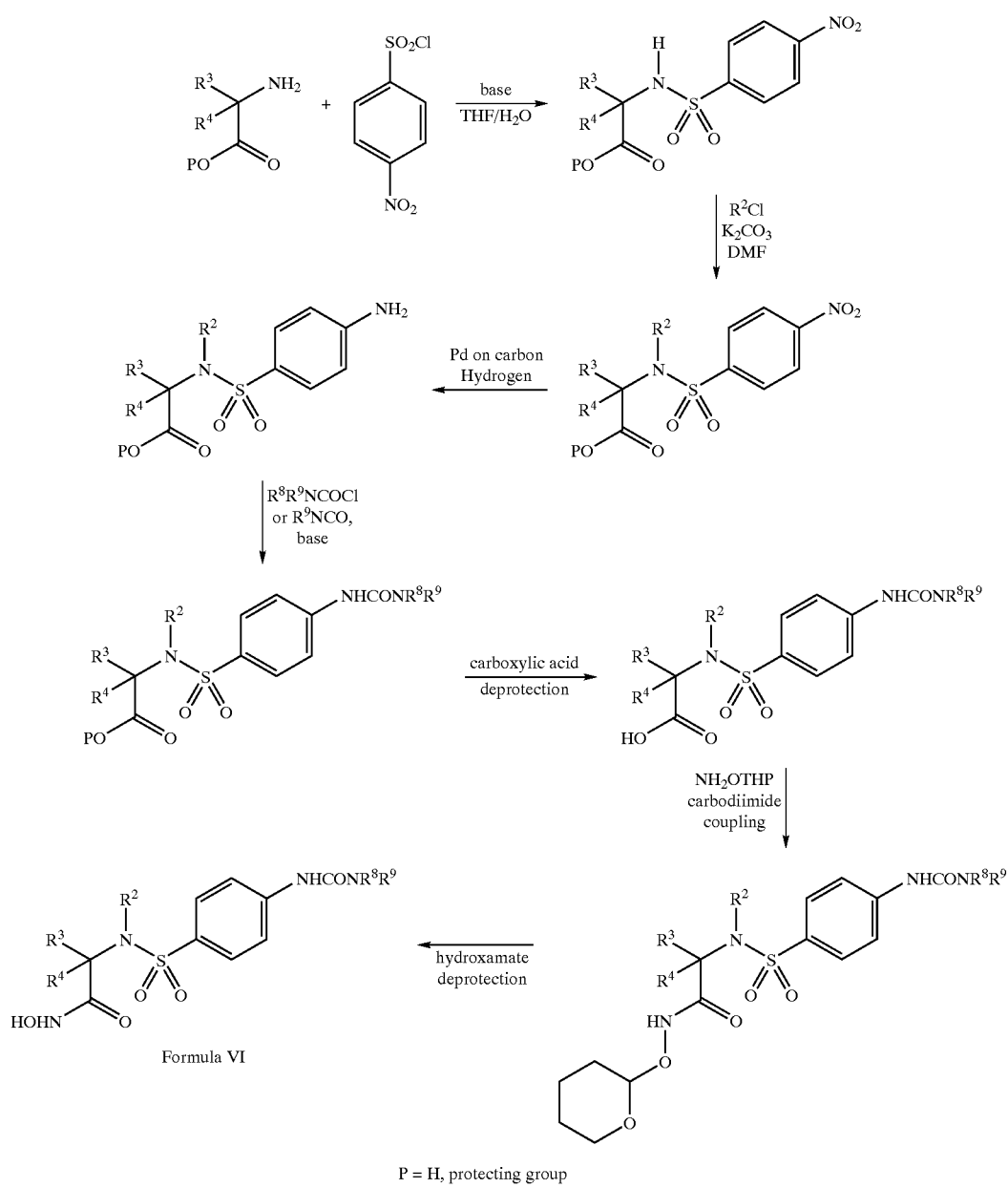
Formula VI
P = H, protecting group Scheme 7

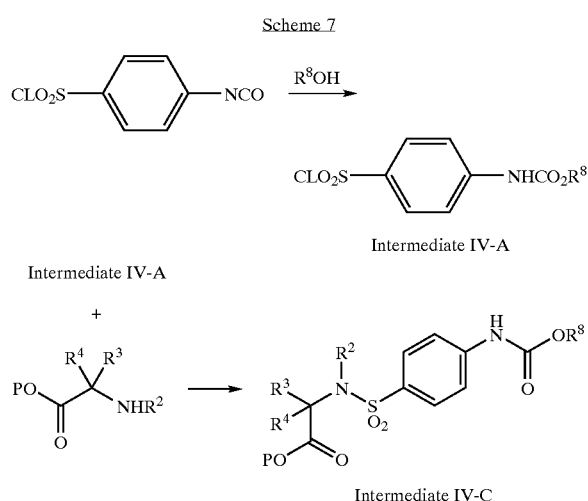

Compounds of the present can possess one or more asymmetric carbon atoms and are thus capable of existing in the form of optical isomers as well as in the form of racemic or nonracemic mixtures thereof. The optical isomers can be obtained by resolution of the racemic mixtures according to conventional processes well known in the art, for example by formation of diastereoisomeric salts by treatment with an optically active acid or base. Examples of appropriate acids are tartaric, diacetyltartaric, dibenzoyltartaric, ditoluoyltartaric and camphorsulfonic acid and then separation of the mixture of diastereoisomers by crystallization followed by liberation of the optically active bases from these salts. A different process for separation of optical isomers involves the use of a chiral chromatography column optimally chosen to maximize the separation of the enantiomers. Still another available method involves synthesis of covalent diastereoisomeric molecules, e.g., esters, amides, acetals, ketals, and the like, by reacting compounds of Formula I with an optically active acid in an activated form, a optically active diol or an optically active isocyanate. The synthesized diastereoisomers can be separated by conventional means such as chromatography, distillation, crystallization or sublimation, and then hydrolyzed to deliver the enantiomerically pure compound. In some cases hydrolysis to the parent optically active drug is not necessary prior to dosing the patient since the compound can behave as a prodrug. The optically active compounds of Formula I can likewise be obtained by utilizing optically active starting materials.

Contemplated equivalents of the general formulas set forth above for the MMP inhibitor compounds and derivatives as well as the intermediates are compounds otherwise corresponding thereto and having the same general properties such as tautomers thereof and compounds wherein one or more of the various R groups are simple variations of the substituents as defined therein, e.g., wherein R is a higher alkyl group than that indicated. In addition, where a substituent is designated as, or can be, a hydrogen, the exact chemical nature of a substituent which is other than hydrogen at that position, e.g., a hydrocarbyl radical or a halogen, hydroxy, amino and the like functional group, is not critical so long as it does not adversely affect the overall activity and/or synthesis procedure. For example, two hydroxyl groups, two amino groups, two thiol groups or a mixture of two hydrogen-heteroatom groups on the same carbon are know not to be stable without protection or as a derivative.

The chemical reactions described above are generally disclosed in terms of their broadest application to the preparation of the compounds of this invention. Occasionally, the reactions may not be applicable as described to each compound include within the disclosed scope. The compounds for which this occurs will be readily recognized by those skilled in the art. In all such cases, either the reactions can be successfully performed by conventional modifications known to those skilled in the art, e.g., by appropriate protection of interfering groups, by changing to alternative conventional reagents, by routine modification of reaction conditions, and the like, or other reactions disclosed herein or otherwise conventional, will be applicable to the preparation of the corresponding compounds of this invention. In all preparative methods, all starting materials are known or can be readily prepared from known starting materials.

d. Treatment Methods

A process for treating a host mammal having a condition associated with pathological matrix metalloproteinase activity is also contemplated. That process comprises administering a metalloproteinase inhibitor described hereinbefore in an MMP enzyme-inhibiting effective amount to a mammalian host having such a condition. The use of administration repeated a plurality of times is particularly contemplated.

A contemplated inhibitor compound is used for treating a host mammal such as a mouse, rat, rabbit, dog, horse, primate such as a monkey, chimpanzee or human that has a condition associated with pathological matrix metalloproteinase activity.

Also contemplated is the similar use of a contemplated metalloproteinase inhibitor compound in the treatment of a disease state that can be affected by the activity of Metalloproteinases such as TNF-α convertase. Exemplary of such disease states are the acute phase responses of shock and sepsis, coagulation responses, hemorrhage and cardiovascular effects, fever and inflammation, anorexia and cachexia.

In treating a disease condition associated with pathological matrix metalloproteinase activity, a contemplated MMP inhibitor compound can be used, where appropriate, in the form of an amine salt derived from an inorganic or organic acid. Exemplary acid salts include but are not limited to the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide, hydroiodide, 2-hydroxy-ethanesulfonate, lactate, maleate, methanesulfonate, nicotinate, 2-naphthalenesulfonate, oxalate, palmoate, pectinate, persulfate, 3-phenylpropionate, picrate, pivalate, propionate, succinate, tartrate, thiocyanate, tosylate, mesylate and undecanoate.

Also, a basic nitrogen-containing group can be quaternized with such agents as lower alkyl ($C_1$–$C_6$) halides, such as methyl, ethyl, propyl, and butyl chloride, bromides, and iodides; dialkyl sulfates like dimethyl, diethyl, dibuytl, and diamyl sulfates, long chain ($C_8$–$C_{20}$) halides such as decyl, lauryl, myristyl and dodecyl chlorides, bromides and iodides, aralkyl halides like benzyl and phenethyl bromides, and others to provide enhanced water-solubility. Water or oil-soluble or dispersible products are thereby obtained as desired. The salts are formed by combining the basic compounds with the desired acid.

Other compounds useful in this invention that are acids can also form salts. Examples include salts with alkali metals or alkaline earth metals, such as sodium, potassium, calcium or magnesium or with organic bases or basic quaternary ammonium salts.

In some cases, the salts can also be used as an aid in the isolation, purification or resolution of the compounds of this invention.

Total daily dose administered to a host mammal in single or divided doses of an MMP enzyme-inhibiting effective amount can be in amounts, for example, of about 0.001 to about 30 mg/kg body weight daily and more usually about 0.01 to about 10 mg. Dosage unit compositions can contain such amounts or submultiples thereof to make up the daily dose. A suitable dose can be administered, in multiple sub-doses per day. Multiple doses per day can also increase the total daily dose, should such dosing be desired by the person prescribing the drug.

The dosage regimen for treating a disease condition with a compound and/or composition of this invention is selected in accordance with a variety of factors, including the type, age, weight, sex, diet and medical condition of the patient, the severity of the disease, the route of administration, pharmacological considerations such as the activity, efficacy, pharmacokinetic and toxicology profiles of the particular compound employed, whether a drug delivery system is utilized and whether the compound is administered as part of a drug combination. Thus, the dosage regimen actually employed can vary widely and therefore can deviate from the preferred dosage regimen set forth above.

A compound useful in the present invention can be formulated as a pharmaceutical composition. Such a composition can then be administered orally, parenterally, by inhalation spray, rectally, or topically in dosage unit formulations containing conventional nontoxic pharmaceutically acceptable carriers, adjuvants, and vehicles as desired. Topical administration can also involve the use of transdermal administration such as transdermal patches or iontophoresis devices. The term parenteral as used herein includes subcutaneous injections, intravenous, intramuscular, intrasternal injection, or infusion techniques. Formulation of drugs is discussed in, for example, Hoover, John E., *Remington's Pharmaceutical Sciences*, Mack Publishing Co., Easton, Pa.; 1975 and Liberman, H. A. and Lachman, L., Eds., *Pharmaceutical Dosage Forms*, Marcel Decker, New York, N.Y., 1980.

Injectable preparations, for example, sterile injectable aqueous or oleaginous suspensions can be formulated according to the known art using suitable dispersing or wetting agents and suspending agents. The sterile injectable preparation can also be a sterile injectable solution or suspension in a nontoxic parenterally acceptable diluent or solvent, for example, as a solution in 1,3-butanediol. Among the acceptable vehicles and solvents that can be employed are water, Ringer's solution, and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid find use in the preparation of injectables. Dimethyl acetamide, surfactants including ionic and non-ionic detergents, polyethylene glycols can be used. Mixtures of solvents and wetting agents such as those discussed above are also useful.

Suppositories for rectal administration of the drug can be prepared by mixing the drug with a suitable nonirritating excipient such as cocoa butter, synthetic mono-, di-, or triglycerides, fatty acids and polyethylene glycols that are sold at ordinary temperatures but liquid at the rectal temperature and will therefore melt in the rectum and release the drug.

Solid dosage forms for oral administration can include capsules, tablets, pills, powders, and granules In such solid dosage forms, the compounds of this invention are ordinarily combined with one or more adjuvants appropriate to the indicated route of administration. If administered per os, the compounds can be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets can contain a controlled-release formulation as can be provided in a dispersion of active compound in hydroxypropylmethyl cellulose. In the case of capsules, tablets, and pills, the dosage forms can also comprise buffering agents such as sodium citrate, magnesium or calcium carbonate or bicarbonate. Tablets and pills can additionally be prepared with enteric coatings.

For therapeutic purposes, formulations for parenteral administration can be in the form of aqueous or non-aqueous isotonic sterile injection solutions or suspensions. These solutions and suspensions can be prepared from sterile powders or granules having one or more of the carriers or diluents mentioned for use in the formulations for oral administration. The compounds can be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

Liquid dosage forms for oral administration can include pharmaceutically acceptable emulsions, solutions, suspensions, syrups, and elixirs containing inert diluents commonly used in the art, such as water. Such compositions can also comprise adjuvants, such as wetting agents, emulsifying and suspending agents, and sweetening, flavoring, and perfuming agents.

The amount of active ingredient that can be combined with the carrier materials to produce a single dosage form varies depending upon the mammalian host treated and the particular mode of administration.

Certain of the sulfonamide, sulfinamide or sulfenamide, compounds of this invention that are administered in accordance with an above-discussed process can serve as prodrugs to other compounds of this invention. Prodrugs are drugs that can be chemically converted in vivo or in vitro by biological systems into an active derivative or derivatives. Prodrugs are administered in essentially the same manner as the other pharmaceutical compounds of the invention.

e. Detailed Preparative and Crystallographic Methods

The starting materials for use in the methods of preparation of the invention are known or can be prepared by conventional methods known to a skilled person or in an analogous manner to processes described in the art.

Generally, the process methods of the present invention can be performed as follows.

EXAMPLE 1

N-[2-(4-morpholinyl)ethyl]-N-[[4-[(4-pentylbenzoyl)amino]phenyl]sulfonyl]-D-valine (IX)

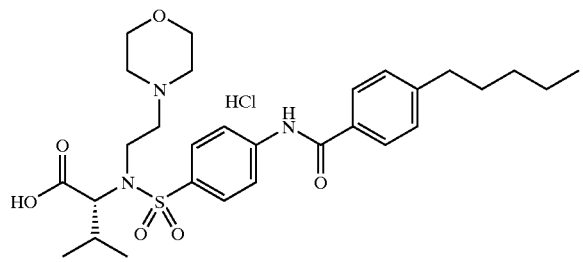

Part A:

To a solution of D-valine (25.0 g, 213 mmol) in $H_2O$ (180 mL) and acetone (96 mL) was added triethylamine (62 mL, 448 mmol) and was cooled to zero degrees Celsius. To this solution was added 4-nitrobenzenesulfonyl chloride (45.3 g, 204 mmol) in acetone (100 mL) dropwise. The solution was stirred for 72 hours. The solution was concentrated in vacuo and the resulting aqueous layer was extracted with toluene and acidified to pH=2 with 2N HCl. The aqueous layer was extracted with ethyl acetate three times and the combined organic layers were washed with saturated NaCl and dried over $MgSO_4$. Concentration in vacuo provided the sulfonamide as a light brown solid (37.15 g, 61%).

Part B:

A solution of the sulfonamide of part A (37.15 g, 123 mmol) and a catalytic amount of $H_2SO_4$ in dichloromethane/dioxane (1 L) was subjected to isobutylene for 18 hours. The solution was cooled to zero degrees Celsius and quenched with saturated $NaHCO_3$. The aqueous layer was extracted with ethyl acetate and the organic layer was washed with saturated NaCl and dried over $MgSO_4$. Chromatography (on silica, ethyl acetate/hexane) provided the t-butyl ester as a solid (16.7 g, 38%).

Part C:

To a solution of the t-butyl ester of part B (16.5 g, 46 mmol) in DMF (60 mL) was added 4-(2-chloroethyl)morpholine hydrochloride (17.2 g, 92 mmol) and $K_2CO_3$ (25.5 g, 184 mmol) and the solution was heated to sixty degrees Celsius for 7 hours. The solution was partitioned between ethyl acetate and $H_2O$ and the organic layer was washed with saturated NaCl and dried over $Na_2SO_4$. Chromatography (on silica, ethyl acetate/hexane) provided the morpholine compound as a solid (21.5 g, 99%).

Part D:

To a solution of the morpholine compound of part C (21.5 g, 45.6 mmol) in THF (200 mL) in a flask purged with $H_2$ was added 4% Pd/C (3.04 g) and the solution was hydrogenated until uptake ceased. The solution was filtered through Celite® to remove the excess catalyst and the filtrate was concentrated in vacuo to provide the aniline as an oil (19.2 g, 95%).

Part E:

To a solution of the aniline of part D (2.60 g, 5.88 mmol) in THF (20 mL) was added triethylamine (3.2 mL, 22.8 mmol) and the solution was cooled to four degrees Celsius. To this solution was added 4-pentylbenzoyl chloride (2.1 g, 10.0 mmol) and the solution was stirred for 18 hours at ambient temperature. The solution was concentrated in vacuo and the residue was partitioned between ethyl acetate and saturated $NaHCO_3$. The organic layer was washed with saturated $NaHCO_3$ and saturated NaCl and dried over $Na_2SO_4$. Chromatography (ethyl acetate/hexane) provided the benzamide as a solid (2.09 g, 58%).

Part F:

A solution of the benzamide of part E (2.09 g, 3.4 mmol) in 4N HCl (20 mL) was stirred for 72 hours. The solution was concentrated in vacuo and the residue was dissolved into ethyl acetate (5 mL) and dropped into ethyl ether. The resulting precipitate was collected by vacuum filtration to provide R-N-[4-[[[1-carboxyl]-2-methylpropyl][2-(4-orpholinyl)ethyl]amino]-sulfonyl]phenyl]-4-pentylbenzamide monohydrochloride as white solid (1.9 g, 94%).

MS(CI) $MH^+$ calculated for $C_{29}H_{41}N_3O_6S$: 560, found: 560.

EXAMPLE 2

R-N-[4-[[[1-(hydroxyamino)carbonyl]-2-methylpropyl][2-(4-morpholinyl)ethyl]amino]-sulfonyl]phenyl]-4-pentylbenzamide, monohydrochloride (X)

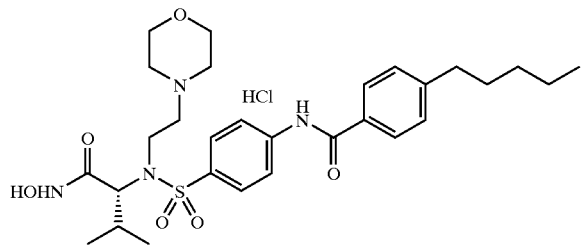

Part A:

To a solution of the acid of Example 1, part F (1.52 g, 2.56 mmol) in DMF (5 mL) was added N-hydroxybenzotriazole (414 mg, 3.07 mmol) and the solution was cooled to four degrees Celsius. To this solution was added 4-methylmorpholine (1.69 mL, 15.6 mmol), 1-(3-dimethylaminopropyl)-3-ethylcarbodiimide hydrochloride (687 mg, 3.58 mmol) and tetrahydropyranyl hydroxylamine (449 mg, 3.84 mmol) and was stirred for 1 hour at ambient temperature. The solution was partitioned between ethyl acetate and saturated $NaHCO_3$ and the organic layer was washed with saturated $NaHCO_3$, saturated NaCl and $H_2O$ and dried over $Na_2SO_4$. Chromatography (ethyl acetate/methanol) provided the ester as a solid (1.54 g, 91%).

Part B:

To a solution of the ester of part A (1.54 g, 2.34 mmol) in methanol (1 mL) was added 4N HCl (10 mL) and the solution was stirred for 18 hours at ambient temperature. The solution was concentrated in vacuo. Reverse phase chromatography (on silica, acetonitrile/$H_2O$ (HCl) provided the title compound, R-N-[4-[[[1-(hydroxyamino)carbonyl]-2-methylpropyl][2-(4-morpholiny)lethyl]amino]sulfonyl]phenyl]-4-pentylbenzamide, monohydrochloride, as a white solid (745 mg, 52%). MS(CI) $MH^+$ calculated for $C_{29}H_{42}N_4O_6S$: 575, found: 575.

EXAMPLE 3

(R)-4-hexyl-N-[4-[[[1-(hydroxyamino)-carbonyl]-2-methylpropyl][2-(4-morpholinyl)ethyl]amino]sulfonyl]-phenylbenzamide, monohydrochloride (XI)

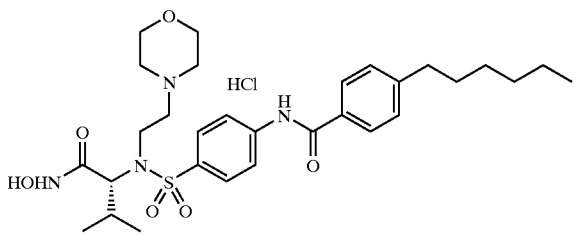

Part A:

To a solution of the aniline of Example 1, part D (2.5 g, 5.7 mmol) was added triethylamine (3.2 mL, 22.8 mmol) and the solution was cooled to four degrees Celsius. To this solution was added 4-hexylbenzoyl chloride (2.18 g, 9.69 mmol) and the solution was stirred overnight at ambient temperature. The solution was concentrated in vacuo and the residue was partitioned between ethyl acetate and saturated $NaHCO_3$. The organic layer was washed with saturated $NaHCO_3$ and saturated NaCl and dried over $Na_2SO_4$. Chromatography (on silica, ethyl acetate/hexane) provided the benzamide as a solid (2.76 g, 77%).

Part B:

A solution of the benzamide of part A (2.7 g, 4.3 mmol) in 4N HCl in dioxane (20 mL) was stirred for 72 hours. The solution was concentrated in vacuo and the residue was dissolved into ethyl acetate (5 mL). This solution was dropped into ethyl ether. The resulting precipitate was collected by vacuum filtration to provide the acid as a solid (2.5 g, 95%).

Part C:

To a solution of the acid of part B (2.03 g, 3.33 mmol) in DMF (5 mL) was added N-hydroxybenzotriazole (540 mg, 4.00 mmol) and the solution was cooled to four degrees Celsius. To this solution was added 4-methylmorpholine (2.19 mL, 20.0 mmol), 1-(3-dimethylaminopropyl)-3-ethylcarbodiimide hydrochloride (894 mg, 4.66 mmol) and tetrahydropyranyl hydroxylamine (615 mg, 5.00 mmol) and the solution was stirred for 1 hour at ambient temperature. The solution was partitioned between ethyl acetate and saturated $NaHCO_3$ and the organic layer was washed with saturated $NaHCO_3$, saturated NaCl and $H_2O$ and dried over $Na_2SO_4$. Chromatography (on silica, ethyl acetate/methanol) provided the ester as a solid (2.01 g, 90%).

Part D:

To a solution of the ester of part C (2.01 g, 3.24 mmol) in methanol (1 mL) was added 4N HCl (10 mL) and the solution was stirred for 18 hours at ambient temperature. Reverse phase chromatography (on silica, acetonitrile/$H_2O$ (0.05% HCl)) provided the title compound, (R)-4-hexyl-N-[4-[[[(1-(hydroxyamino)carbonyl]-2-methylpropyl][2-(4-morpholinyl)ethyl]amino]sulfonyl]-phenylbenzamide, monohydrochloride, as a white solid (1.23 g, 61%). MS(CI) $MH^+$ calculated for $C_{30}H_{44}N_4O_6S$: 589, found: 589.

EXAMPLE 4

Cloning, Expression and Purification of the Catalytic Domain of MMP-8

The MMP-8 catalytic domain was cloned by PCR amplification from a cDNA contruct of full-length MMP-8. The amplified DNA was cloned into NdeI/HindIII restriction sites in an in-house pRec expression vector. Protein was expressed in a bacterial expression system by induction with nalidixic acid. Recombinant protein was expressed primarily as inclusion bodies. Purified protein was recovered in high yield following ion exchange chromatography of denatured protein. Refolding from denaturant and subsequent purification using a second ion exchange step resulted in active protein that was used for crystallography.

Crystallization of Inhibitor Complexes

Crystals were grown by vapor equilibration in sitting drops following a procedure similar to that described by Bode et al. ("The X-ray crystal structure of the catalytic domain of human neutrophil collagenase inhibited by a substrate analogue reveals the essentials for catalysis and specificity," *FEBS Letters* 338, 227–233 (1994).) A solution of the enzyme inhibitor complex is mixed with a precipitating reagent to form the sitting drop which is equilibrated against a high-salt solution. Slow dehydration of the drop leads to formation of single crystals of the inhibitor complex. Details are below.

Protein:

12 mg/ml MMP-8 in 10 mM MES pH 6.0, 100 mM NaCl, 5 mM $CaCl_2$ pre-incubated with 1 mM inhibitor for 10 minutes at ambient temperature.

Sitting Drop:

4 ul of the protein-inhibitor complex mixed with 6.8 ul 10% PEG6000 and 0.2 M MES pH 6.0

Reservoir:

0.8 to 2.5 M sodium/potassium phosphate pH 6.0 (not mixed with protein/inhibitor/PEG drop).

X-ray Data Collection

Intensities from crystals of the enzyme inhibitor complexes were measured on a MAR image plate at −140° C. X-rays were generated from a rotating anode generator using a Cu target. The $CuK_\alpha$ X-rays were focused onto the samples using long Pt and Ni mirrors.

The data were integrated and scaled using the program DENZO (Otwinowski, Z. and Minor W. in *Proceedings of CCP4 Study Weekend: Data Collection and Processing* (eds. Sawyer, L., Issacs, N., and Bailey, S.) pp. 56–62 (SERC Daresbury Laboratories, Warrington, UK 1993)).

The structures for compounds XIV and XV are shown below. Compound XIV is described in U.S. patent application Ser. No. 09/254,535, herein incorporated by reference. Compound XV is described in U.S. patent application Ser. No. 09/254,530, herein incorporated by reference.

Formula XIV

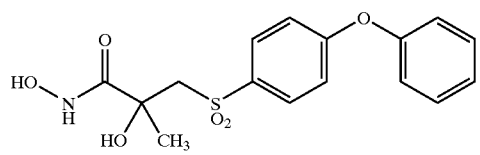

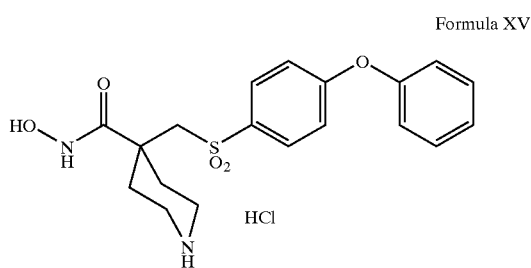

Formula XV

Statistics for six data sets are given in the Tables II and III below:

Space Group: $P2_1 2_1 2_1$

TABLE II

Compound with which MMP-8 catalytic domain (residues 85–242) are complexed[a]

| complexed[a] | a[b] | b[b] | c[b] | Resolution[c] | Rsym[d] | I/sig[e] |
|---|---|---|---|---|---|---|
| XII | 32.97 | 68.92 | 70.61 | 1.65 | 0.050(0.209) | 21.8(3.4) |
| IX | 33.05 | 68.59 | 68.55 | 1.64 | 0.078(0.326) | 10.9(1.7) |
| X | 33.50 | 68.79 | 69.34 | 1.65 | 0.084(0.257) | 12.4(2.7) |
| XI | 33.31 | 68.50 | 67.01 | 1.83 | 0.097(0.467) | 14.2(2.9) |
| XIV | 32.43 | 68.16 | 72.08 | 1.46 | 0.029(0.078) | 25.6(11.9) |
| XV | 32.40 | 68.26 | 71.70 | 1.43 | 0.079(0.307) | 15.9(2.4) |

TABLE III

Compound with which MMP-8 catalytic domain (residues 85–242) are complexed[a]

| complexed[a] | total[f] | unique[g] | redundant[h] | coverage[i] |
|---|---|---|---|---|
| XII | 52840 | 18220 | 2.9 | 90.7(66.8) |
| IX | 42171 | 17815 | 2.4 | 90.9(76.1) |
| X | 39481 | 15999 | 2.5 | 87.2(80.6) |
| XI | 46758 | 14042 | 3.3 | 97.6(97.3) |
| XIV | 70996 | 26770 | 2.5 | 93.8(82.5) |
| XV | 107545 | 29122 | 3.7 | 96.4(87.3) |

[a]Inhibitor code;
[b]lattice constants (unit cell dimensions).
[c]data resolution;
[d]Rsym (internal consistency) for overall and highest resolution shell;
[e]I/sigma (signal/noise ratio) for overall and highest resolution shell;
[f]total number of observations collected;
[g]number of unique reflections;
[h]redundancy;
[i]data coverage (completeness in %) for overall and highest resolution shell.

Structure Solution and Model Building and Refinement

Coordinates of the structure of MMP-8 in complex with batimastat (4-(N-hydroxyamino)-2R-isobutyl-2S-(2-thienylthiomethyl)succinyl-L-phenylalanine-N-methylamide) were obtained from the Protein Data Bank (accession number: 1 mmb) Coordinates of only the protein atoms and the metal ions were used in an initial refinement with the X-ray data collected on the new complexes. Standard simulated annealing protocols in the program XPLOR (Brünger, A. T. (1993). *XPLOR (Version 3.1): A System for X-ray Crystallography and NMR* (Yale University Press, New Haven, Conn.)) were used. The refined positional and thermal parameters were used to calculate new phases for display of Fo-Fc and 2Fo-Fc electron density maps; the program XPLOR was also used for calculation of the maps which were displayed on a Silicon Graphics terminal using the program O (Jones, T. A., Zou, J. Y., Cowan, S. W. and Kjeldgarrd, M. (1991). "Improved methods for binding protein models in electron density maps and the location of errors in these models," *Acta Crystallogr*. A47, 110–119).

New electron density at the expected active site could in all cases be interpreted with flexible, three-dimensional models of the inhibitors as generated in the program INSIGHTII (Biosym Technologies (1993). Insight II User Guide, Version 2.2.0. San Diego). Solvent positions were also identified from these electron density maps and side chains of the protein were also sometimes manually adjusted.

Final refinements of the structure were carried out with inclusion of inhibitor and solvent ligands. In the refinements, 10% of the data was set aside for cross validation by evaluation of $R_{free}$ (A. T. Brünger, "Free R Value: a novel statistical quantity for accessing the accuracy of crystal structures," *Nature* 355, 472–475 (1992)). Results are shown in the Table IV.

TABLE IV

Compound with which MMP-8 catalytic domain (residues 85–242) is complexed[a]

| complexed[a] | Resolution[j] | $R_{free}$/$R_{work}$[k] | Reflection[m] | rms Bond[n] | rms Angle[p] |
|---|---|---|---|---|---|
| XII | 8.00–1.65 | 0.249(0.290)/0.187(0.284) | 17419 | 0.01 | 1.6 |
| IX | 8.00–1.64 | 0.286(0.370)/0.188(0.323) | 15052 | 0.01 | 1.7 |
| X | 8.00–1.69 | 0.276(0.283)/0.195(0.271) | 14239 | 0.02 | 2.0 |
| XI | 8.00–1.83 | 0.262(0.376)/0.168(0.225) | 12019 | 0.02 | 1.9 |
| XIV | 8.00–1.46 | 0.222(0.215)/0.181(0.215) | 26180 | 0.01 | 1.7 |
| XV | 8.00–1.43 | 0.208(0.232)/0.174(0.247) | 26617 | 0.01 | 1.7 |

[a]Inhibitor code.
[j]resolution (in angstroms).
[k]number of reflections.
[m]$R_{work}$/$R_{free}$ for overall and highest resolution shell
[n]RMS deviation in bond lengths (in angstroms).
[p]RMS deviation in covalent bond angles (in degrees).

In the case of Formula XIII, we noticed that the refinement yielded an unexpected conformation for the side chain of Arg 222. Display of the electron density maps verified the new position for this residue. Analysis of the structure also revealed that retention of the previously observed conformation of this residue would have led to steric clash with the P1' moiety of the inhibitor.

In the cases of Formulas IX, X and XI, the refinement yielded a completely new position for Tyr 227 in addition to the perturbed Arg 222 side chain. The new Tyr position was resulted from a major movement backbone and sidechains for residues 224–229. Display of the electron density maps verified the new position for this residue. Analysis of the structure also revealed that retention of the previously observed conformations of this residues would have led to steric clash between the side chain of Tyr 227 and the P1' moiety of the inhibitor.

The combination of the swerve of Arg 222 side chain and the conformation changes in residues 224–229 essentially opens up the enzyme S1' pocket. In this new form, inhibitors with longer (equivalent to seven and more carbon chains beyond the second ring) and bigger P1' (—$CF_3$, —($C_6H_4$)—, etc.) moieties can be accommodated. Two factors govern the inhibitor P1' moiety: it has to be nonpolar (a single polar —$NH_2$ group has been shown tolerable) to pass through the highly hydrophobic S1' pocket of the enzyme and it has to have some exposed polar groups when the chain is long enough to protrude itself out to the hydrophilic solvent region.

The examples herein can be performed by substituting the generically or specifically described reactants and/or operating conditions of this invention for those used in the preceding examples.

The invention being thus described, it is apparent that the same can be varied in many ways. Such variations are not to be regarded as a departure from the spirit and scope of the present invention, and all such modifications and equivalents as would be obvious to one skilled in the art are intended to be included within the scope of the following claims.

What is claimed is:

1. A compound; an enantiomer, diastereomer, racemate, or tautomer of the compound; or a salt of the compound, enantiomer, diastereomer, racemate, or tautomer, wherein:
the compound has the following structure:

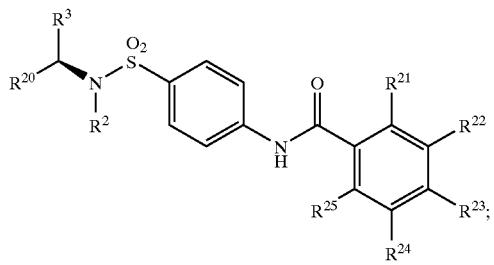

$R^2$ is morpholinylalkyl;
$R^3$ is selected from the group consisting of H, alkyl, alkenyl, alkynyl, cycloalkyl, haloalkyl, alkylaryl, arylalkyl, alkoxy, alkoxyalkyl, hydroxyalkyl, aminoalkyl, alkylaminoalkyl, haloalkoxy, and haloalkylthio;
$R^{20}$ is selected from the group consisting of —C(O)OH, —SH, and —C(O)SH; and
$R^{21}$, $R^{22}$, $R^{23}$, $R^{24}$, and $R^{25}$ are independently selected from the group consisting of H, $C_1$ to about $C_{20}$ alkyl, $C_1$ to about $C_{20}$ alkenyl, $C_1$ to about $C_{20}$ alkynyl, cycloalkyl, haloalkyl, alkoxyalkyl, hydroxyalkyl, aminoalkyl, alkylaminoalkyl, nitroalkyl, alkoxy, cycloalkoxy, alkoxycarbonyl, alkoxyalkyl, haloalkoxy, haloalkylthio, alkylamino, and carboxyalkyl.

2. The compound, enantiomer, diastereomer, racemate, tautomer, or salt of claim 1 wherein $R^{20}$ is —C(O)OH.

3. The compound, enantiomer, diastereomer, racemate, tautomer, or salt of claim 2 wherein $R^{21}$ and $R^{25}$ are H.

4. The compound, enantiomer, diastereomer, racemate, tautomer, or salt of claim 3 wherein $R^{22}$ and $R^{24}$ are H.

5. The compound, enantiomer, diastereomer, racemate, tautomer, or salt of claim 4 wherein $R^{23}$ is $C_1$ to about $C_{20}$ alkyl.

6. The compound, enantiomer, diastereomer, racemate, tautomer, or salt of claim 5 wherein $R^{23}$ is $C_1$ to about $C_{20}$ linear alkyl.

7. The compound, enantiomer, diastereomer, racemate, tautomer, or salt of claim 2 wherein $R^3$ is selected from the group consisting of alkyl, alkenyl, alkynyl, haloalkoxy, and haloalkylthio.

8. The compound, enantiomer, diastereomer, racemate, tautomer, or salt of claim 7 wherein $R^2$ is 2-(N-morpholino)ethyl.

9. The compound, enantiomer, diastereomer, racemate, tautomer, or salt of claim 6 wherein $R^3$ is selected from the group consisting of alkyl, alkenyl, alkynyl, haloalkoxy, and haloalkylthio.

10. The compound, enantiomer, diastereomer, racemate, tautomer, or salt of claim 6 wherein $R^2$ is 2-(N-morpholino)ethyl.

11. The compound, enantiomer, diastereomer, racemate, tautomer, or salt of claim 8 wherein the compound has the following structure:

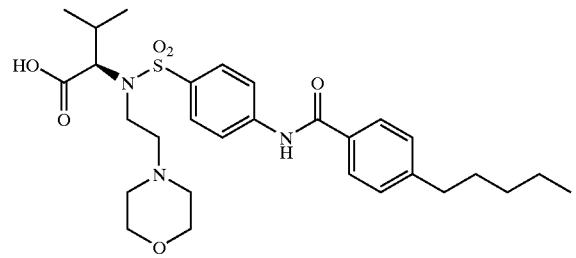

12. A method of inhibiting a matrix metalloproteinase, wherein:
the method comprises contacting the matrix metalloproteinase with a compound; an enantiomer, diastereomer, racemate, or tautomer of the compound; or a salt of the compound, enantiomer, diastereomer, racemate, or tautomer;
the compound has the following formula:

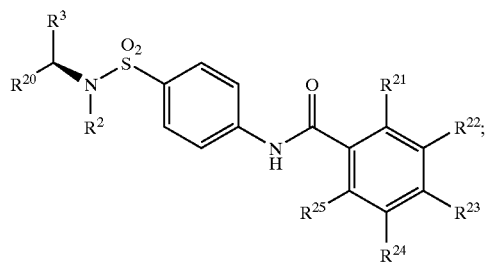

$R^2$ is morpholinylalkyl;
$R^3$ is selected from the group consisting of H, alkyl, alkenyl, alkynyl, cycloalkyl, haloalkyl, alkylaryl, arylalkyl, alkoxy, alkoxyalkyl, hydroxyalkyl, aminoalkyl, alkylaminoalkyl, haloalkoxy, and haloalkylthio;
$R^{20}$ is selected from the group consisting of —C(O)OH, —SH, and —C(O)OSH; and $R^{21}$, $R^{22}$, $R^{23}$, $R^{24}$, and $R^{25}$ are independently selected from the group consisting of H, $C_1$ to about $C_{20}$ alkyl, $C_1$ to about $C_{20}$ alkenyl, $C_1$ to about $C_{20}$ alkynyl, cycloalkyl, haloalkyl, alkoxyalkyl, hydroxyalkyl, aminoalkyl, alkylaminoalkyl, nitroalkyl, alkoxy, cycloalkoxy, alkoxycarbonyl, alkoxyalkyl, haloalkoxy, haloalkylthio, alkylamino, and carboxyalkyl.

13. The method of claim 12 wherein $R^{20}$ is —C(O)OH.

14. The method of claim 12 wherein $R^3$ is selected from the group consisting of H, alkyl, alkenyl, alkynyl, haloalkoxy, and haloalkylthio.

15. The method of claim 14 wherein $R^3$ is a $C_1$ to about $C_{12}$ alkyl.

16. The method of claim 15 wherein $R^3$ is a $C_1$ to about $C_4$ alkyl.

17. The method of claim 16 wherein $R^3$ is isopropyl.

18. The method of claim 12 wherein $R^2$ is 2-(N-morpholino)ethyl.

19. The method of claim 12 wherein $R^{21}$ and $R^{25}$ are H.

20. The method of claim 19 wherein $R^{22}$ and $R^{24}$ are H.

21. The method of claim 20 wherein $R^{23}$ is $C_1$ to about $C_{20}$ alkyl.

22. The method of claim 21 wherein $R^{23}$ is methyl or $C_2$ to about $C_{20}$ linear alkyl.

23. The method of claim 22 wherein $R^{23}$ is n-pentyl or n-hexyl.

24. The method of claim 23 wherein the compound has the following structure:

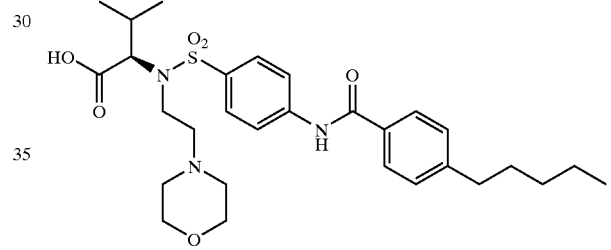

25. The method of claim 12 wherein the matrix metalloproteinase is MMP-8.

26. The method of claim 12 wherein the matrix metalloproteinase is MMP-13.

27. A method treating osteoarthritis in a mammal, wherein:
the method comprises providing to the mammal an osteoarthritis-treating-effective amount of a compound; an enantiomer, diastereomer, racemate, or tautomer of the compound; or a salt of the compound, enantiomer, diastereomer, racemate, or tautomer;
the compound has the following formula:

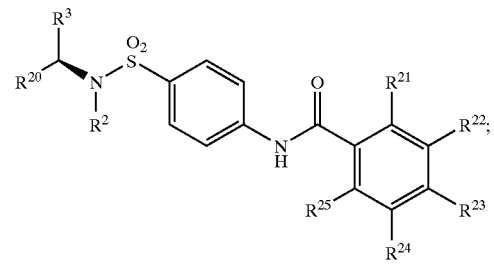

$R^2$ is morpholinylalkyl;
$R^3$ is selected from the group consisting of H, alkyl, alkenyl, alkynyl, cycloalkyl, haloalkyl, alkylaryl, arylalkyl, alkoxy, alkoxyalkyl, hydroxyalkyl, aminoalkyl, alkylaminoalkyl, haloalkoxy, and haloalkylthio;

$R^{20}$ is selected from the group consisting of —C(O)OH, —SH, and —C(O)SH; and $R^{21}$, $R^{22}$, $R^{23}$, $R^{24}$, and $R^{25}$ are independently selected from the group consisting of H, $C_1$ to about $C_{20}$ alkyl, $C_1$ to about $C_{20}$ alkenyl, $C_1$ to about $C_{20}$ alkynyl, cycloalkyl, haloalkyl, alkoxyalkyl, hydroxyalkyl, aminoalkyl, alkylaminoalkyl, nitroalkyl, alkoxy, cycloalkoxy, alkoxycarbonyl, alkoxyalkyl, haloalkoxy, haloalkylthio, alkylamino, and carboxyalkyl.

28. The method of claim 27 wherein the mammal is a human.

29. The method of claim 28 wherein the compound has the following structure:

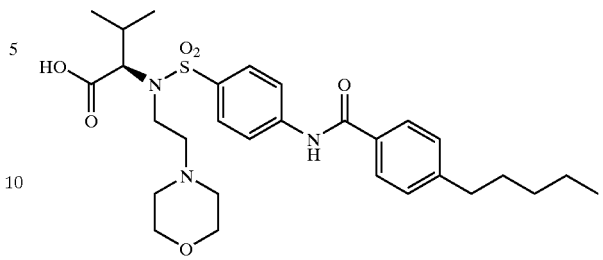

* * * * *

SEQUENCE LISTING

<160> NUMBER OF SEQ ID NOS: 3

<210> SEQ ID NO 1
<211> LENGTH: 158
<212> TYPE: PRT
<213> ORGANISM: human

<400> SEQUENCE: 1

```
Asn Pro Lys Trp Glu Arg Thr Asn Leu Thr Tyr Arg Ile Arg Asn Tyr
1               5                   10                  15

Thr Pro Gln Leu Ser Glu Ala Glu Val Glu Arg Ala Ile Lys Asp Ala
            20                  25                  30

Phe Glu Leu Trp Ser Val Ala Ser Pro Leu Ile Phe Thr Arg Ile Ser
        35                  40                  45

Gln Gly Glu Ala Asp Ile Asn Ile Ala Phe Tyr Gln Arg Asp His Gly
    50                  55                  60

Asp Asn Ser Pro Phe Asp Gly Pro Asn Gly Ile Leu Ala His Ala Phe
65                  70                  75                  80

Gln Pro Gly Gln Gly Ile Gly Gly Asp Ala His Phe Asp Ala Glu Glu
                85                  90                  95

Thr Trp Thr Asn Thr Ser Ala Asn Tyr Asn Leu Phe Leu Val Ala Ala
            100                 105                 110

His Glu Phe Gly His Ser Leu Gly Leu Ala His Ser Ser Asp Pro Gly
        115                 120                 125

Ala Leu Met Tyr Pro Asn Tyr Ala Phe Arg Glu Thr Ser Asn Tyr Ser
    130                 135                 140

Leu Pro Gln Asp Asp Ile Asp Gly Ile Gln Ala Ile Tyr Gly
145                 150                 155
```

<210> SEQ ID NO 2
<211> LENGTH: 159
<212> TYPE: PRT
<213> ORGANISM: human

<400> SEQUENCE: 2

```
Ile Pro Lys Trp Arg Lys Thr His Leu Thr Tyr Arg Ile Val Asn Tyr
1               5                   10                  15

Thr Pro Asp Leu Pro Lys Asp Ala Val Asp Ser Ala Val Glu Lys Ala
            20                  25                  30

Leu Lys Val Trp Glu Glu Val Thr Pro Leu Thr Phe Ser Arg Leu Tyr
        35                  40                  45

Glu Gly Glu Ala Asp Ile Met Ile Ser Phe Ala Val Arg Glu His Gly
    50                  55                  60
```

-continued

```
Asp Phe Tyr Pro Phe Asp Gly Pro Gly Asn Val Leu Ala His Ala Tyr
65                  70                  75                  80

Ala Pro Gly Pro Gly Ile Asn Gly Asp Ala His Phe Asp Asp Asp Glu
                85                  90                  95

Gln Trp Thr Lys Asp Thr Thr Gly Thr Asn Leu Phe Leu Val Ala Ala
                100                 105                 110

His Glu Ile Gly His Ser Leu Gly Leu Phe His Ser Ala Asn Thr Glu
            115                 120                 125

Ala Leu Met Tyr Pro Leu Tyr His Ser Leu Thr Asp Leu Thr Arg Phe
            130                 135                 140

Arg Leu Ser Gln Asp Asp Ile Asn Gly Ile Gln Ser Leu Tyr Gly
145                 150                 155

<210> SEQ ID NO 3
<211> LENGTH: 156
<212> TYPE: PRT
<213> ORGANISM: human

<400> SEQUENCE: 3

Asn Pro Arg Trp Glu Gln Thr His Leu Thr Tyr Arg Ile Glu Asn Tyr
1               5                   10                  15

Thr Pro Asp Leu Pro Arg Ala Asp Val Asp His Ala Ile Glu Lys Ala
                20                  25                  30

Phe Gln Leu Trp Ser Asn Val Thr Pro Leu Thr Phe Thr Lys Val Ser
            35                  40                  45

Glu Gly Gln Ala Asp Ile Met Ile Ser Phe Val Arg Gly Asp His Arg
    50                  55                  60

Asp Asn Ser Pro Phe Asp Gly Pro Gly Gly Asn Leu Ala His Ala Phe
65                  70                  75                  80

Gln Pro Gly Pro Gly Ile Gly Gly Asp Ala His Phe Asp Glu Asp Glu
                85                  90                  95

Arg Trp Thr Asn Asn Phe Arg Glu Tyr Asn Leu His Arg Val Ala Ala
                100                 105                 110

His Glu Leu Gly His Ser Leu Gly Leu Ser His Ser Thr Asp Ile Gly
            115                 120                 125

Ala Leu Met Tyr Pro Ser Tyr Thr Phe Ser Gly Asp Val Gln Leu Ala
            130                 135                 140

Gln Asp Asp Ile Asp Gly Ile Gln Ala Ile Tyr Gly
145                 150                 155
```